(12) United States Patent
Acland et al.

(10) Patent No.: US 7,811,761 B2
(45) Date of Patent: Oct. 12, 2010

(54) METHOD FOR IDENTIFYING PROGRESSIVE ROD-CONE DEGENERATION IN DOGS

(75) Inventors: Gregory M. Acland, Kennett Square, PA (US); Gustavo D. Aguirre, Philadelphia, PA (US); Orly Goldstein, Ithaca, NY (US); Barbara Zangerl, Philadelphia, PA (US); Susan Pearce-Kelling, Berkshire, NY (US); Duska J. Sidjanin, Brookfield, WI (US); Jeanette S. Felix, Horseheads, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/638,072

(22) Filed: Dec. 13, 2006

(65) Prior Publication Data
US 2007/0161033 A1 Jul. 12, 2007

Related U.S. Application Data

(60) Provisional application No. 60/750,433, filed on Dec. 14, 2005.

(51) Int. Cl.
*C07H 21/04* (2006.01)
*C12Q 1/68* (2006.01)
(52) U.S. Cl. .................... 435/6; 435/91.1; 435/91.2; 536/23.1; 536/24.3
(58) Field of Classification Search ................ None
See application file for complete search history.

(56) References Cited

U.S. PATENT DOCUMENTS

| 5,804,388 | A | 9/1998 | Aguirre et al. |
| 6,428,958 | B1 | 8/2002 | Aguirre et al. |
| 7,312,037 | B2 * | 12/2007 | Aguirre et al. ............. 435/6 |
| 2003/0092019 | A1 * | 5/2003 | Meyer et al. ............. 435/6 |

FOREIGN PATENT DOCUMENTS

EP 1 609 876 A1 12/2005

OTHER PUBLICATIONS

Goldstein et al. (Genomics, vol. 88, pp. 541-550, 2006).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Tacher et al. (J. of Heredity, vol. 96, No. 7, pp. 812-816, 2005.*
Thisted (May 1998).*
Sidjanin, et al.; Radiation hybrid map, physical map, and low-pass genomic sequence of the canine *prcd* region on CFA9 and comparative mapping with the syntenic region on human chromosome 17; Genomics 81 (2003); pp. 138-148.
Kijas, et al.; Cloning of the canine ABCA4 gene and evaluation in canine cone-rod dystrophies and progressive retinal atrophies; Molecular Vision, Mar. 2004, vol. 10; pp. 223-232; XP-002429576.
Gu, et al.; Evaluation of the APOH Gene as a Positional Candidate for *prcd* in Dogs; Investigative Ophthalmology & Visual Science, May 1999; vol. 40, No. 6; pp. 1229-1237; XP009082167.
Lindblad-Toh, et al.; Genome sequence, comparative analysis and haplotype structure of the domestic dog; Nature, Dec. 2005, vol. 438, No. 7069; pp. 803-819; XP-002429578.
Gu, et al.; Identification of a RAPD marker linked to progressive rod-cone degeneration in dogs; Mammalian Genome, Sep. 1998, vol. 9, No. 9; pp. 740-744; XP-002429575.
Lin, et al.; Isolation and Investigation of Canine Phosducin as a Candidate for Canine Generalized Progressive Retinal Atrophies; Exp. Eye Res., Oct. 1998, vol. 67, No. 4; pp. 473-480; XP-002429577.
Casse, et al.; KIAA1753, a Gene Potentially Involved in Progressive Rod-cone Degeneration (prcd); Invest Ophthalmol Vis Sci, 2003; vol. 44; E-Abstract 2318; 1 page; XP008051751.
Goldstein; et al.; Linkage Disequilibrium Map of the Progressive Rod Cone Degeneration Interval; Invest Ophthalmol Vis Sci, Apr. 2004; vol. 45, No. Suppl. 2; E-Abstract 4756; 1 page; XP009082168.
Goldstein, et al.; Linkage disequilibrium mapping in domestic dog breeds narrows the progressive rod-cone degeneration interval and identifies ancestral disease-transmitting chromosome; Genomics, Nov. 2006, vol. 88, No. 5; pp. 541-550; XP-002429579.

* cited by examiner

*Primary Examiner*—Jeanine A Goldberg
(74) *Attorney, Agent, or Firm*—Hodgson Russ LLP

(57) ABSTRACT

Provided is a method for identifying dogs as likely to be genetically normal, carriers of, or affected with progressive rod-cone degeneration comprising analyzing nucleic acids from a dog and determining the presence or absence of one or more prcd polymorphisms in the nucleic acids. Representative prcd polymorphisms characteristic of a prcd haplotype are also provided.

6 Claims, 18 Drawing Sheets

Figure 5

| No. | Gene | Amplicon | Primers | Product size | BAC | CFA9 location | SNP location | Alleles | Affected alleles observed |
|---|---|---|---|---|---|---|---|---|---|
| 1 | GRB2 | a | CGTCACCCCTGTGAACCGGA (SEQ ID NO: 1) GGTCACCAGTGACCCAGCC (SEQ ID NO: 2) | 158 | 122J4 | 8177527 8177684 | 8177621 | A/G | A/G |
| 2 | GRB2 | e | CAAAGTCAAAGAGGGCCTGGACG (SEQ ID NO: 3) CTTAGGACCTGTAAGGATTAA (SEQ ID NO: 4) | 195 | 122J4 | 8177208 8177402 | 8177229 | A/G | A/G |
| 3 | GRB2 | b | CAAAGTCAAAGAGGGCATGACG (SEQ ID NO: 5) GGGGCGCTCCACCTTATTT (SEQ ID NO: 6) | 447 | 122J4 | 8176956 8177402 | 8177123 | A/G | A/G |
| 4 | GRB2 | d | GGGCTGCGTCCTGGCTATCTG (SEQ ID NO: 7) CTTCCCGTCGTCACTGGTCATCAT (SEQ ID NO: 8) | 210 | 122J4 | 8175987 8176196 | 8176052-060 | d1/d2 | d1/d2 |
| 5 | | K9STS6 | GGTCTGAGCACTGCTATGGC (SEQ ID NO: 9) GCTGCGGTGATGGAAGTTCTC (SEQ ID NO: 10) | 696 | 275K3/ 338A17 | 7509354 7510049 | 7509853 | T/C | C |
| 6 | RNF157 | K9STS27 | AGAGGTCACAGGGCTCTTACAG (SEQ ID NO: 11) TCCACTCCTACAGTGTGGTCA (SEQ ID NO: 12) | 870 | 275K3/ 338A17 | 7503455 7504324 | 7503761 | A/G | A/G |
| 7 | RNF157 | K9STS4 | GAATGTTCCATAGTACCTGAGG (SEQ ID NO: 13) GCTCTGTACCTGTACCTCTTATG (SEQ ID NO: 14) | 593 | 275K3/ 338A17 | 7495018 7495610 | 7495110 | C/T | C |
| 8 | RNF157 | K9STS24 | CTCAGAGAACATTCCACCAG (SEQ ID NO: 15) GCAAGAACGCTCATCGTCCTCT (SEQ ID NO: 16) | 1030 | 275K3/ 338A17 | 7494419 7495448 | 7494524 | A/G | G |
| 9 | RNF157 | K9STS7 | GTGTGCCGAGGAAGTGAAGAC (SEQ ID NO: 17) CATGGCCTCCAAGCATCCAG (SEQ ID NO: 18) | 864 | 338A17 | 7486627 7487490 | 7486815 | A/G | A/G |
| 10 | | | | | | | 7486678 | A/G | G |
| 11 | RNF157 | K9STS13 | ATGCCTGTATAGGTCAGTTC (SEQ ID NO: 19) CTCAATCCATTCTGCTGCCA (SEQ ID NO: 20) | 714 | 338A17 | 7482401 7483114 | 7482730-751 | (AG)11 /12 | (AG)11/1 2 |
| 12 | | K9STS20 | GGGACTCATAATACAGCCTTAC (SEQ ID NO: 21) TCAGTATCAACGTGGCAACC (SEQ ID NO: 22) | 749 | 338A17 | 7440956 7441704 | 7441217 | A/G | A |
| 13 | | K9STS18 | TTCGGACTGTCAACCACTGAGAG (SEQ ID NO: 23) CCTAGGACCCGATGAGGATT (SEQ ID NO: 24) | 654 | 338A17 | 7431115 7431768 | 7431355 | C/T | C/T |

Figure 5 continued

| | | | | | | | |
|---|---|---|---|---|---|---|---|
| 14 | FAM100B | | | | 7431167 | A/G | A/G |
| 15 | | G07 | CCAGGAAAGGCCAGAGAGCATC (SEQ ID NO: 25) GTGGCCGTGGAGAATCAGAACC (SEQ ID NO: 26) | 405 | 388A17/ 262H18 | 7409140 7409544 | 7409331 | C/T | C/T |
| 16 | PRPSAP1 | PRPSAP1 | CTGATAGAGCCTAGACCCACTG (SEQ ID NO: 27) CCTGAAATGGAGTTACAGTGAG (SEQ ID NO: 28) | 405 | 262H18 | 7331415 7331819 | 7331626 | G/C | G/C |
| 17 | | | | | | | 7331616 | C/T | C/T |
| 18 | E2-230K | E2-230K exon18 | GGTGAGTTTGATGCTGAAGTGC (SEQ ID NO: 29) GCAGCTCCCTGGTTCTCATTC (SEQ ID NO: 30) | 568 | 262H18 | 7307564 7308131 | 7307885 | G del | G/del |
| 19 | E2-230K | E2-230K int1 | TATGATCCGCAGGCTTGTGTG (SEQ ID NO: 31) ACATTCAAACGGTTTCTCGCAG (SEQ ID NO: 32) | 621 | 262H18 | 7295258 7295878 | 7295425 | C/T | C/T |
| 20 | AANAT | AANAT | AGGTCACGGGACACCTGCTGT (SEQ ID NO: 33) GTATCTGGACGAGATCAAGCAC (SEQ ID NO: 34) | 929 | 262H18/ 10M13 | 7237092 7238020 | 7237330 | A/G | A/G |
| 21 | RHBDL6 | FLJ22341 exon 17 | GAAGCACCACATAGTGTGG (SEQ ID NO: 35) ACTCCAGGAGCTTGCAGCATGAA (SEQ ID NO: 36) | 507 | 262H18/ 10M13 | 7233874 7234380 | 7234259 | C/T | C |
| 22 | RHBDL6 | FLJ22341 intron4 | GGAAATCACGCTAGGGTTCATC (SEQ ID NO: 37) GCACTGTGACTTTACATGGCAC (SEQ ID NO: 38) | 515 | 262H18/ 10M13 | 7228133 7228647 | 7228625 | A/G | G |
| 23 | | 13c44 F5/R5 | GGTGCTGGTTTCTCAGGACAG (SEQ ID NO: 39) CAGGACGGGTCACGTCTTTAG (SEQ ID NO: 40) | 806 | 262H18/ 10M13 | 7222317 7223122 | 7222842 | T/C | T |
| 24 | | 13c44 F4/R4 | GTTCCTGTATGTCCTAGACTTG (SEQ ID NO: 41) CTGCAGAGACATCTGCCTGTG (SEQ ID NO: 42) | 903 | 262H18/ 10M13 | 7221067 7221969 | 7221808 | T/C | C |
| 25 | | | | | | | 7221638 | C/G | C |

Figure 5 continued

| | | | | | | | |
|---|---|---|---|---|---|---|---|
| 26 | | 13c44 F1/R1 | CAGCACAGACTGCATTGCTTC (SEQ ID NO: 43)<br>TGGGACAGAAAGTGTCACCTC (SEQ ID NO: 44) | 806 | 262H18/<br>10M13 | 7218321/<br>7219126 | 7218637 | C/T | T |
| 27 | *RHBDL6* | K9STS44 | CACCTAGATTTCAGATTCCTGG (SEQ ID NO: 45)<br>CAAGAGGATTGCCCTCTATTAGG (SEQ ID NO: 46) | 773 | 262H18/<br>10M13 | 7217364/<br>7218136 | 7217935 | A/G | A |
| 28 | | | | | | | 7217631 | A/G | G |
| 29 | | | | | | | 7217488 | C/T | C/T |
| 30 | | | | | | | 7217437 | C/T | T |
| 31 | | K9STS43 | TTTGCCTCACCAGTTCCAGG (SEQ ID NO: 47)<br>AAACCTGACTTCCCAGAACC (SEQ ID NO: 48) | 620 | 10M13 | 7216486/<br>7217105 | 7216945 | C/A | C |
| 32 | | | | | | | 7216898 | A/G | G |
| 33 | | | | | | | 7216687 | A/G | G |
| 34 | | 13c43b611-<br>1514 | TGGAAACTCACCTGGTCTCTG (SEQ ID NO: 49)<br>TAGGCCATGTCCTCTTGCTGC (SEQ ID NO: 50) | 904 | 10M13 | 7210041/<br>7210944 | 7210843 | A/C | A |
| 35 | | | | | | | 7210738 | CTG ins | no ins |
| 36 | | | | | | | 7210406 | T/C | T |
| 37 | | K9STS49 | AACCTCTCTGAACCTTGATGAG (SEQ ID NO: 51)<br>GTGGCTCAGTTCAGTTAGGTGTC (SEQ ID NO: 52) | 889 | 10M13 | 7207872/<br>7208760 | 7208710 | A/G | G |
| 38 | | | | | | | 7208091 | A/C | A |
| 39 | | SINE | GGTGACCGGGGTGGCTCAGTCA (SEQ ID NO: 53)<br>TCAGAACCTTCTTGAGTTTGC (SEQ ID NO: 54) | 741 | 10M13 | 7208025/<br>7208769 | 7208069 | SINE ins | no ins |
| 40 | | K9STS48 | GGATATGGGCTCTAGAATACC (SEQ ID NO: 55)<br>GAATAGAGCTGGGTACTGTACC (SEQ ID NO: 56) | 945 | 10M13 | 7206894/<br>7207838 | 7207658 | C/T | C |
| 41 | | | | | | | 7207599 | C/T | T |
| 42 | | | | | | | 7207443 | C/T | T |

Figure 5 continued

| # | Gene | Marker | Sequence | | | | | | |
|---|---|---|---|---|---|---|---|---|---|
| 43 | | | | | | | 7207437 | A/G | A |
| 44 | | | | | | | 7207376 | A/G | G |
| 45 | | K9STS45 | GCCTAGATGGCTCAGTCAGT (SEQ ID NO: 57)<br>TCAGGGTCTCTTGTGAGGCT (SEQ ID NO: 58) | 827 | 10M13 | 7204102<br>7204928 | 7204396 | A/G | A |
| 46 | | K9STS41 | TATATGCCAGACACTCGCTGG (SEQ ID NO: 59)<br>CAGATCTCAGTTCAGGATAGAG (SEQ ID NO: 60) | 709 | 10M13 | 7202338<br>7203046 | 7202668 | A/G | G |
| 47 | | | | | | | 7202448 | A/G | G |
| 48 | CYGB | 13c37b607-1536 | GAGCACCCTTCCTTTCTCAAG (SEQ ID NO: 61)<br>CAGTGTGCGACAGGATGACAG (SEQ ID NO: 62) | 929 | 10M13 | 7199035<br>7199964 | 7199890 | C/G | C |
| 49 | | | | | | | 7199635 | A/G | A |
| 50 | | | | | | | 7199442 | A/G | A |
| 51 | | | | | | | 7199297 | G del | no del |
| 52 | | | | | | | 7199220 | G/A | G |
| 53 | CYGB | K9STS38 | GGCATCTGGCCTGTCATCACT (SEQ ID NO: 63)<br>CGAGTTCTGAAGACCCTCCTT (SEQ ID NO: 64) | 957 | 10M13 | 7198217<br>7199173 | 7198687 | A/G | A |
| 54 | | | | | | | 7198397 | C/T | C |
| 55 | | | | | | | 7198360 | C/T | T |
| 56 | CYGB | CYGB | GACGAGTCAGGGATTCTTCA (SEQ ID NO: 65)<br>TGAGGTCACGCAGCAGGTTC (SEQ ID NO: 66) | 355 | 10M13 | 7197932<br>7198286 | 7198172 | A/G | A |
| 57 | CYGB | CYGB intron 3 | ACCCGTAAGCAGCAGAGACAGTTC (SEQ ID NO: 67)<br>CACCCCAGGAGAGTAGAAATC (SEQ ID NO: 68) | 914 | 10M13 | 7196711<br>7197624 | 7197446 | T/C | T |
| 58 | | | | | | | 7197441 | T/C | T |
| 59 | | | | | | | 7196969 | C/T | T |
| 60 | | | | | | | 7196805 | C/G | C |
| 61 | | | | | | | 7196755 | TGCC ins | no ins |
| 62 | CYGB | K9STS40 | TCACTGCCTGCCGAGCTGTAG (SEQ ID NO: 69)<br>TCAGCCAATGCTGACCAGTGCT (SEQ ID NO: 70) | 720 | 10M13 | 7196047<br>7196766 | 7196432 | T/C | T |
| 63 | | | | | | | 7196147 | C/T | C |

Figure 5 continued

| # | Gene | Name | Sequence | Size | 10M13 | Pos1 | Pos2 | Variant | Allele |
|---|---|---|---|---|---|---|---|---|---|
| 64 | | | | | | | 7196119 | T/C | T |
| 65 | CYGB | 31F5 | CCTGGTGTGAGTCCGTCATTAC (SEQ ID NO: 71) AGGAACTCCTCTCACACTTTTG (SEQ ID NO: 72) | 898 | 10M13 | 7192869 7193766 | 7192970 | A/C | A |
| 66 | CYGB | 31F4 | CCACTCGATAGTTCACAGATAC (SEQ ID NO: 73) CCTGGGACTGTCATTCCTCAG (SEQ ID NO: 74) | 775 | 10M13 | 7192093 7192867 | 7192187 | A/G | A |
| 67 | | 13c36b7782-1142 | TGGGAATGGGGTAGACAAAT (SEQ ID NO: 75) AATGAAGCCAGAAAGACAAGG (SEQ ID NO: 76) | 856 | 10M13 | 7187285 7188140 | 7188086 | A/G | A |
| 68 | | | | | | | 7187723 | C/T | C |
| 69 | | 13c36b1708-1856 | GACCCCTTGACACCGCTTCCATCT (SEQ ID NO: 77) GCCACTGCTGCCCATCCTGAG (SEQ ID NO: 78) | 990 | 10M13 | 7186789 7187778 | 7187157 | C/G | C |
| 70 | | | | | | | 7187009 | C/T | C |
| 71 | | poly3 | CCAGTGGCAGCAGGAACC (SEQ ID NO: 79) CCGACCTGCTGCCCACGACTG (SEQ ID NO: 80) | 512 | 10M13 | 7186315 7186826 | 7186710 | A/G | A |
| 72 | | i1 | CTCTTCCTACTCAGCACCTTG (SEQ ID NO: 81) CCCAGACTCTGCCTTACCTG (SEQ ID NO: 82) | 430 | 10M13 | 7186273 7186702 | 7186373-5 | CTT del | no del |
| 73 | | i2-1 | GCAGCAGGTCGGAGAGAGAC (SEQ ID NO: 83) GGAGCCCAAGGGCATCATGTG (SEQ ID NO: 84) | 830 | 10M13 | 7185497 7186326 | 7186154 | C ins | no ins |
| 74 | | | | | | | 7186097 | C/G | C |
| 75 | | | | | | | 7185596 | G/A | A |
| 76 | | i2-2 | CTCTCAACTCTAGTGAGACAAAG (SEQ ID NO: 85) CAGGGAGGACTAGTCATTCAAG (SEQ ID NO: 86) | 459 | 10M13 | 7185082 7185540 | 7185419 | C/T | T |
| 77 | | | | | | | 7185408 | TCC ins | no ins |
| 78 | | | | | | | 7185405 | A/G | A |
| 79 | | | | | | | 7185344-52 | 7 nt del | no del |
| 80 | | | | | | | 7185302 | C/T | C |
| 81 | | | | | | | 7185271 | G/A | G |
| 82 | | | | | | | 7185243 | C/T | C |

Figure 5 continued

| | | | | | | |
|---|---|---|---|---|---|---|
| 83 | p9 | CAAAGGTGAAATGATGAGCACTG (SEQ ID NO: 87)<br>TCAGCTGGAATTTGTGACTGTG (SEQ ID NO: 88) | 755 | 10M13 | 7184392<br>7185146 | 7184893 | G/A | G |
| 84 | e3-3U | CTGATTTCCTGGCTGCTCCTACCC (SEQ ID NO: 89)<br>TTAACTAGCTGATGACATGGAC (SEQ ID NO: 90) | 972 | 10M13 | 7183424<br>7184395 | 7184208 | C/T | C |
| 85 | | | | | | 7184041 | C/G | G |
| 86 | | | | | | 7183553 | G/A | G |
| 87 | e5a | GAAATGCCAGCTGGGATCTGTG (SEQ ID NO: 91)<br>CTTCCCTCAGATGTGGAGTCAG (SEQ ID NO: 92) | 509 | 10M13 | 7182623<br>7183131 | 7182768 | A/G | G |
| 88 | p8 | CTGACTCCACATCTGAGGGAAG (SEQ ID NO: 93)<br>GGAAGGTGTAAACACAATCTGC (SEQ ID NO: 94) | 763 | 10M13 | 7181882<br>7182644 | 7182314 | T/G | G |
| 89 | i6a | CTGTTCTAGGGACCTGCTCAG (SEQ ID NO: 95)<br>CTCTCTCGGCCCTCTCTCTCTG (SEQ ID NO: 96) | 585 | 10M13 | 7181525<br>7182109 | 7181758 | A/C | A |
| 90 | | | | | | 7181694 | G ins | no ins |
| 91 | 13c34F4/R4 | ACAGCTAGTCCTTTACCTCCTC (SEQ ID NO: 97)<br>CCACCTCATTAGCTCTCTGGTC (SEQ ID NO: 98) | 487 | 10M13 | 7180739<br>7181225 | 7181060 | C/T | T |
| 92 | | | | | | 7180983 | A/T | T |
| 93 | | | | | | 7180830 | A/C | A |
| 94 | | | | | | 7180774 | A/G | G |
| 95 | oldF | ACCCCGCCCATCCGAACT (SEQ ID NO: 99)<br>CAGGATGTCCTCGAGGCCCAG (SEQ ID NO: 100) | 503 | 10M13 | 7180137<br>7180639 | 7180158 | A/G | A |
| 96 | p7 | ATGGGAACATGACCAGAGAGC (SEQ ID NO: 101)<br>GCATATGTATCCCACAGAGAG (SEQ ID NO: 102) | 1084 | 10M13 | 7179687<br>7180770 | 7179783 | C/T | C |
| 97 | p6 | GATGTGGTGCAGGGCTTTAAGGAG (SEQ ID NO: 103)<br>GGAGAGATGCCATTGATGTGTG (SEQ ID NO: 104) | 979 | 10M13 | 7178807<br>7179785 | 7179170 | G del | no del |
| 98 | | | | | | 7179036 | A/G | G |
| 99 | 13C39b510-548 | GACTGCAGTGGTCTCTGTTCAG (SEQ ID NO: 105)<br>CTCCTGTGTCAATACCTCCTC (SEQ ID NO: 106) | 1489 | 10M13 | 7177412<br>7178900 | 7177787 | A/G | A |
| 100 | | | | | | 7177749 | A/C | A |

Figure 5 continued

| | | | | | | |
|---|---|---|---|---|---|---|
| 101 | p5 | ACTGTTGCAGCTTCTCAGGTG (SEQ ID NO: 107)<br>TGATTTATGGAGGACTGACTGTC (SEQ ID NO: 108) | 861 | 10M13 | 7176603<br>7177463 | 7177162 | A/T | A |
| 102 | 13c39b1809-<br>2488 | CTGTGACCCGTTCTTTCAGAG (SEQ ID NO: 109)<br>TAGAGCCCCCTACCTTCAGAC (SEQ ID NO: 110) | 680 | 10M13 | 7175809<br>7176488 | 7175842 | A/G | A |
| 103 | 13c39b2893 | AAATCATCCTGTGTTTCACTG (SEQ ID NO: 111)<br>CATGGATCTGTATTCACTGACAC (SEQ ID NO: 112) | 906 | 10M13 | 7175032<br>7175937 | 7175404 | A/G | A |
| 104 | repeat | ACTCAAGTGTCCCAGACCTCG (SEQ ID NO: 113)<br>GGGAGTTCAGAGCTGTGGAG (SEQ ID NO: 114) | 190 | 10M13 | 7174797<br>7174986 | 7174862 | 1/2/3/4 | 2 |
| 105 | 13c39F/R | GCTCTTCTACTAGGTGTCCTG (SEQ ID NO: 115)<br>CAGAGTCTGGTTGTTGTTATTCCTC (SEQ ID NO: 116) | 876 | 10M13 | 7172394<br>7173269 | 7173092 | C/T | C |
| 106 | | | | | | 7172778 | A/G | G |
| 107 | | | | | | 7172766 | A/T | A |
| 108 | | | | | | 7172680 | C/T | T |
| 109 | 13c39b7340-<br>8106 | TCTCAACATCGCGATAACTCTC (SEQ ID NO: 117)<br>CCACCATCTCGACTTTCTCAC (SEQ ID NO: 118) | 771 | 10M13 | 7170293<br>7171063 | 7170923 | C/T | T |
| 110 | | | | | | 7170716 | C ins<br>1 G del/3<br>G dels<br>T del | no ins<br>1 G del |
| 111 | | | | | | 7170689 | | |
| 112 | | | | | | 7170451 | | no del |
| 113 | 39-96 | GTGACCAGAAGTGAGAAAGTC (SEQ ID NO: 119)<br>GTGCGTCCACGTGTTCCTAAG (SEQ ID NO: 120) | 285 | 10M13 | 7170039<br>7170323 | 7170231 | A/G | A |
| 114 | 13c24 | ATGGCAGATTCTGTGGAAGTG (SEQ ID NO: 121)<br>AGACCAGACTCATGGACACTG (SEQ ID NO: 122) | 981 | 10M13 | 7167646<br>7168626 | 7168133 | C/T | C |
| 115 | p2 | GAATCCGGTCTACCCTGCTAAG (SEQ ID NO: 123)<br>GCATTCAGGATGGTCTCAAGTAG (SEQ ID NO: 124) | 1263 | 10M13 | 7165325<br>7166587 | 7165468 | A/C | A |
| 116 | ST6GalNac2-<br>NaeI | CAGTGCCACAATCCTGAGATCAG (SEQ ID NO: 125)<br>CACGACTACACAGCTACTTTGAA (SEQ ID NO: 126) | 635 | 10M13 | 7164337<br>7164971 | 7164625 | T/C | T |

Figure 5 continued

| | | | | | | | |
|---|---|---|---|---|---|---|---|
| 117 | | AGTAAAGGTCACTGTCAGATGGCC (SEQ ID NO: 127) CACGACTACACAGCTACTTGAA (SEQ ID NO: 128) | 258 | | | A/G | G |
| 118 | ST6GalNa c2 | ST6GalNac2-AvaI | | | | | |
| | | 13c38b3211-3910 | | | | | |
| | | TCTGGCTGGGAGTGTGTTTG (SEQ ID NO: 129) GGTTCTTGTCACTTCACACATC (SEQ ID NO: 130) | 700 | 10M13 | 7162863 7163562 | 7163247 | C/T | C |
| 119 | | | | | | 7163118 | A/G | A/G |
| 120 | ST6GalNa c2 | STHM299-597 AGCACTGAGACAGGACGGTTG (SEQ ID NO: 131) GATTCGTGACCACGTATTGAG (SEQ ID NO: 132) | 923 | 10M13 | 7158529 7159451 | 7159153 | C/T | C |
| 121 | | | | | | 7158855 | C/T | C |
| 122 | ST6GalNa c2 | 13c41b2085-2915 GTCCGAGGGATGAAGATGTAG (SEQ ID NO: 133) CCCAGTTACCAGAATACTGCTC (SEQ ID NO: 134) | 830 | 10M13 | 7157898 7158727 | 7158550 | T ins | no ins |
| 123 | | | | | | 7158401 | C/T | T |
| 124 | | | | | | 7158389 | C del | C del |
| 125 | | | | | | 7158064 | G del | no del |
| 126 | ST6GalNa c2 | ST6GalNac2 exon 4 CCATTAACTTCCACCCTGAGCC (SEQ ID NO: 135) GGTGAAGCCAAAGTTCCAGTAG (SEQ ID NO: 136) | 563 | 10M13 | 7156662 7157224 | 7156718 | C/T | T |
| 127 | ST6GalNa c2 | ST6GalNac2 int 2 CCTCTGGATGGCCAGGTCAAGTG (SEQ ID NO: 137) GTTGATTCCTAGGGCTTCTGAAG (SEQ ID NO: 138) | 865 | 10M13 | 7155106 7155970 | 7155722 | A/G | G |
| 128 | ST6GalNa c1 | ST6GalNac1 CGTTCAACGGAACAGACAGTG (SEQ ID NO: 139) AAACCAGCTTCCCATCTCCTG (SEQ ID NO: 140) | 846 | 10M13 | 7110342 7111187 | 7110867 | A/G | A/G |
| 129 | | 13c40 F2/R2 CACCCAGGACCTAAACCTTTG (SEQ ID NO: 141) GAAGTCCTCACAACAGTATTATG (SEQ ID NO: 142) | 790 | 10M13 | 7108550 7109339 | 7108899 | 1/2/3/4 | 1/2/3/4 |
| 130 | | 36604c34 F/R GAAGTGCAGGTCACTCACCAG (SEQ ID NO: 143) CAGGAGTCAACATGAAAGATTC (SEQ ID NO: 144) | 776 | 36604 | 7083421 7084196 | 7083486 | C/T | C/T |
| 131 | | | | | | 7083473 | C/T | C/T |
| 132 | | FLJ39789 GCTATGGGAGGTAAACTCAAG (SEQ ID NO: 145) GTCAATTTGAAGCGGGTTCTG (SEQ ID NO: 146) | 775 | 36604 | 7074656 7075430 | 7074814 | C/A | C/A |
| 133 | ET | ET1 AACCTCAAATTCGTAGCCAAG (SEQ ID NO: 147) GGTGTCTACGGAACGTGTATTG (SEQ ID NO: 148) | 547 | 36604 | 7005916 7006462 | 7006044 | G del | G del/ no del |

Figure 5 continued

| # | Gene | Marker | Primer | Size | Contig | Position 1 | Position 2 | SNP | SNP | SNP |
|---|------|--------|--------|------|--------|-----------|-----------|-----|-----|-----|
| 134 | ET | ET2 | CACAGAGAGACCCCACTAACTC (SEQ ID NO: 149) / GATCCTATGACAGAGGCATATAG (SEQ ID NO: 150) | 1172 | 36604 | 7001851 | 7002687 | C/T | C/T | C/T |
| 135 | | | | | | 7003022 | 7002664 | | A/G | A/G |
| 136 | | | | | | | 7002361 | | A/C | A/G |
| 137 | | 36604c49 F/R | CTGAGGTTCCTTCCATGTCTG (SEQ ID NO: 151) / GACTGCCAGGAAGAAGTGGTG (SEQ ID NO: 152) | 980 | 36604 | 6991054 / 6992033 | 6991244 | A/C | A/C | A/C |
| 138 | | 36604c13 F/R | CAACATCAACTGGATGTCATAC (SEQ ID NO: 153) / CATAGCTTTAAGATGGAGGCTG (SEQ ID NO: 154) | 583 | 36604 | 6987245 / 6987827 | 6987343 | T/C | T/C | T/C |
| 139 | AK055500 | ST6-4 | GAGATACTTTCATGACTGCCAC (SEQ ID NO: 155) / GGTAAGGCACGTGTGTCTTAG (SEQ ID NO: 156) | 531 | 36604 | 6985116 / 6985646 | 6985287 | A/G | A/G | A/G |
| 140 | | | | | | | 6985286 | | C/T | C/T |
| 141 | AK055500 | 36604c42 F/R | AGGTAGGGTACAGCAAGTTC (SEQ ID NO: 157) / CAGAATGATCCAGCCCAGATG (SEQ ID NO: 158) | 988 | 36604 | 6983020 / 6984007 | 6983898 | A/G | A/G | A/G |
| 142 | | | | | | | 6983813 | | A/G | A/G |
| 143 | | | | | | | 6983303 | | A/G | A/G |
| 144 | AK055500 | 36604c48 F/R | GTGGGTACCTCCTTTGGTGTG (SEQ ID NO: 159) / ACAGGGAAATTCACCTAAGTTGC (SEQ ID NO: 160) | 855 | 36604 | 6978667 / 6979521 | 6979428 | T/C | T/C | T/C |
| 145 | | | | | | | 6979414 | | A/G | A/G |
| 146 | | | | | | | 6979411 | | G/T | G/T |
| 147 | | | | | | | 6978753 | | C/T | C/T |
| 148 | SEC14L | K9STS73 | GGGTTGCGTAACCATGACACA (SEQ ID NO: 161) / GATCCTCATCCTAGTAAGAG (SEQ ID NO: 162) | 885 | 10P17 | 6766844 / 6767728 | 6767180 | A/G | A/G | A/G |
| 149 | | | | | | | 6767024 | | A/G | A/C |
| 150 | SEC14L | K9STS54 | ATCTATTCTGTGCTGTCCTGG (SEQ ID NO: 163) / CTCCACCACTACAGTTACACATAC (SEQ ID NO: 164) | 1226 | 10P17 | 6729618 / 6730843 | 6730719 | G/T | A/C | A/C |
| 151 | SEC14L | K9STS61 | TGCAAACTGTAGATTGCATC (SEQ ID NO: 165) / TCAGTGTATGCCAAGGGTTCAG (SEQ ID NO: 166) | 830 | 10P17 | 6701173 / 6702002 | 6701526 | T/C | T/C | T/C |

Figure 5 continued

| | | | | | | | | | |
|---|---|---|---|---|---|---|---|---|---|
| 152 | SEC14L | K9STS62 | GAAGGCATAACATTCGTGCC (SEQ ID NO: 167) GTACCATAAATACAGCAACATCC (SEQ ID NO: 168) | 1004 | 10P17 | 6697542 6698545 | 6698054 | C/G | G |
| 153 | | | | | | | 6697729 | A/G | A/G |
| 154 | SEC14L | K9STS63 | CCACTACAGGAGAGCTGCTTG (SEQ ID NO: 169) CCTTTACTAAATGATGCCAGTAC (SEQ ID NO: 170) | 959 | 10P17 | 6696093 6697051 | 6696964 | T/G | T |
| 155 | | | | | | | 6696503 | G/A | G |
| 156 | | | | | | | 6696341 | G/A | G |
| 157 | SEC14L | K9STS64 | GCACTAGTGTACTGTTAAGTGTG (SEQ ID NO: 171) AAGAGCACACAGCCCGTGCTGCT (SEQ ID NO: 172) | 915 | 10P17 | 6694391 6695305 | 6695066 | A/G | A/G |
| 158 | SEC14L | K9STS68 | TACCTGATAGTTCGACCGAAGA (SEQ ID NO: 173) CTCGTGGATAGTACGTGTAGT (SEQ ID NO: 174) | 443 | 10P17 | 6691428 6691870 | 6691830 | A/G | A/G |
| 159 | SEC14L | K9STS67 | TCACTAGACAGCACACTTGCA (SEQ ID NO: 175) TCTGCAGTGTTCCAGAAGGTAG (SEQ ID NO: 176) | 766 | 10P17 | 6690543 6691308 | 6690574 | A/T | A/T |
| 160 | SEC14L | K9STS60 | AGCATGGCATTCTTGGATTGGC (SEQ ID NO: 177) AGTCAGGGCATGGACAGTAGG (SEQ ID NO: 178) | 902 | 10P17 | 6681453 6682353 | 6682138 | A/G | A/G |
| 161 | | | | | | | 6682136 | A/G | A/G |

Figure 6A

| Region | # | Gene | prcd-affected MP-NSDTR (PT5) | | prcd-affected ACD (5525) | | prcd-Beagle MB-Beagle (P-827) | | prcd-carrier LR (L13) | | purebred dogs of other breeds not affected with prcd BC (BC9) | | Basenji (3156) | | ESS (Patsy) | | GoIT (4327) | | EM (5516) | | Papillon (PAP15) | |
|---|---|---|---|---|---|---|---|---|---|---|---|---|---|---|---|---|---|---|---|---|---|---|
| | | | H1 | H2 | H2 | H2 | H1 | H2 | H1 | H1 | H2 | H2 | | | H1 | H1 | H1 | H3 | | | H3 | H3 |
| 1 | 1 | GRB2 | G | G | G | G | | | | | A | A | - | - | A | A | A | A | - | - | | |
| | 2 | RNF157 | C | T | T | T | C | C | C | C | C | C | C | C | C | C | C | C | C | C | C | C |
| | 3 | RNF157 | C | C | C | C | C | C | C | C | C | C | C | C | T | C | C | C | C | C | C | C |
| | 4 | RNF157 | C | C | C | C | T | T | O | C | T | T | T | T | T | T | C | C | C | T | C | C |
| | 5 | RNF157 | | | C | T | T | T | C | T | T | T | C | T | C | T | | | T | C | | |
| | 6 | | | | C | C | C | C | | | T | T | C | C | | | | | | | | |
| | 7 | RNF157 | 11 | 11 | 12 | 12 | 11 | 11 | 11 | 11 | 11 | 11 | 11 | 11 | 11 | 11 | 11 | 11 | 11 | 11 | 11 | 11 |
| | 8 | RNF157 | A | A | A | A | A | A | A | A | G | G | A | A | A | A | A | A | A | G | A | A |
| | 9 | RNF157 | T | C | C | C | T | C | T | T | T | T | C | C | C | T | C | C | T | T | C | C |
| | 10 | | G | A | A | A | G | A | G | G | G | G | A | A | A | A | A | A | G | G | A | A |
| 2 | 11 | AANAT | A | A | A | A | A | A | A | A | A | A | G | G | G | G | G | G | G | G | G | G |
| | 12 | RHBDL6 | T | T | T | T | T | T | T | T | C | C | C | C | C | C | C | C | T | T | T | T |
| | 13 | | C | C | C | C | C | C | C | C | C | C | T | C | C | C | C | C | T | C | C | C |
| | 14 | | A | A | A | A | A | A | A | A | T | T | G | G | G | G | G | G | G | G | G | G |
| | 15 | | G | G | G | G | G | G | G | G | T | T | C | C | C | C | C | C | C | C | C | C |
| | 16 | | C | C | C | C | C | C | C | C | T | T | T | T | T | T | T | T | T | T | T | T |
| | 17 | | C | C | C | C | C | C | C | C | T | T | T | T | T | T | C | C | C | C | C | C |
| | 18 | | C | C | C | C | C | C | C | C | T | T | T | T | | | T | T | T | T | | |
| | 19 | | T | T | T | T | T | T | | | G | G | G | G | G | G | T | T | T | G | | |
| | 20 | | G | G | G | G | G | G | G | G | A | A | G | G | A | A | G | G | G | G | G | G |
| | 21 | | A | A | A | A | A | A | A | A | G | G | A | A | G | G | A | A | A | A | A | A |
| | 22 | | A | A | A | A | A | A | A | A | G | G | T | T | G | G | A | A | A | A | A | A |
| | 23 | | T | T | T | T | T | T | T | T | T | T | T | T | C | T | T | T | T | T | T | T |
| | 24 | | C | C | C | C | C | C | C | C | T | T | C | C | T | T | C | C | C | C | C | C |

Figure 6A continued

| # | Gene | | | | | | | | | | | | | | | | | | |
|---|------|---|---|---|---|---|---|---|---|---|---|---|---|---|---|---|---|---|---|
| 25 | | T | C | C | C | C | C | C | C | C | T | C | C | C | C | T | T | | |
| 26 | | C | C | C | T | C | C | T | T | C | C | C | T | T | | | | | |
| 27 | | C | C | C | T | T | C | C | T | C | T | T | C | C | | | | | |
| 28 | CYGB | A | A | A | A | A | G | G | A | A | A | G | A | A | A | A | A | | |
| 29 | | C | C | C | C | C | T | T | T | C | C | T | C | C | | | | | |
| 30 | CYGB | T | T | T | T | T | C | C | C | T | T | C | T | T | | | | | |
| 31 | | A | A | A | A | A | | | | | A | | | | | | | | |
| 32 | | G | G | G | G | G | | | | | G | | | | | | | | |
| 33 | | A | A | A | A | A | | | | | A | | | | | | | | |
| 34 | SEC14L | T | T | C | C | T | C | C | C | T | T | T | C | T | T | T | T | | |
| 35 | SEC14L | T | T | C | C | T | C | C | C | T | T | T | C | T | T | T | T | | |
| 36 | SEC14L | A | A | A | A | A | A | A | C | A | A | A | A | A | A | A | | | |
| 37 | SEC14L | T | T | T | T | T | T | T | T | T | T | T | T | T | T | T | | | |
| 38 | SEC14L | G | G | G | G | G | G | G | G | G | G | G | G | G | G | G | | | |
| 39 | | A | G | G | G | G | A | A | A | G | G | G | A | G | G | G | | | |
| 40 | SEC14L | T | T | T | T | T | T | T | T | T | T | T | T | T | T | T | | | |
| 41 | | | | | | G | G | G | G | G | G | G | G | | G | | | | |
| 42 | | A | G | G | G | G | A | A | A | G | G | G | A | A | G | G | | | |
| 43 | SEC14L | C | T | T | T | T | T | T | T | T | T | T | T | T | T | C | C | | |
| 44 | SEC14L | A | A | A | A | A | A | A | A | A | A | A | C | A | A | A | A | | |
| 45 | SEC14L | A | G | G | G | T | A | A | A | G | G | G | A | A | G | A | A | | |
| 46 | SEC14L | G | G | G | G | A | G | G | G | G | G | G | G | G | G | G | G | | |
| 47 | | A | A | A | A | A | A | A | A | A | G | A | A | A | A | A | A | | |

Figure 6B

| Number | Gene | | prcd-affected | | | | Purebred dog not affected with prcd |
|---|---|---|---|---|---|---|---|
| | | MP-NSDTR (PT5) | ACD (5525) | CBR (V2981) | PWD (PWD14) | BC | BC (BC9) |
| 1 | | G | A | A | | | G | G |
| 2 | PRPSAP1 | C | C | T | C | C | C | C |
| 3 | | G | C | C | C | C | C | C |
| 4 | E2-230K | C | T | T | T | T | T | T |
| 5 | E2-230K | del | C | C | del | del | C | C |
| | LD region / AANAT | A | G | G | G | G | G | G |
| | RHBDL6 | A | A | A | A | A | A | A |
| | CYGB | A | A | A | A | A | G | G |
| | ST6GalNac2 | T | T | T | T | T | G | G |
| 6 | ST6GalNac1 | A | A | A | A | A | C | C |
| 7 | | A | A | G | A | A | A | A |
| | | 4 | 1 | 2 | 4 | 4 | | |
| 8 | | A | A | G | A | A | G | G |
| 9 | | G | G | A | A | G | G | A |
| 10 | | G | G | T | G | G | G | G |
| 11 | ET | del | del | G | del | del | G | G |
| 12 | ET | C | C | T | C | C | T | T |
| 13 | | T | T | C | T | T | T | C |
| 14 | | G | G | T | G | G | G | C |
| 15 | | G | T | A | G | G | G | A |
| 16 | | T | G | A | G | G | G | G |
| 17 | AK055500 | G | A | A | G | G | A | A |
| 18 | | C | C | T | C | C | T | T |

Figure 6B continued

| | | | | | | | | | | | |
|---|---|---|---|---|---|---|---|---|---|---|---|
| 19 | AK055500 | A | A | G | G | A | A | A | A | G | G |
| 20 | | G | G | A | A | G | G | G | G | A | A |
| 21 | AK055500 | A | A | G | G | A | A | A | A | G | G |
| 22 | | C | G | T | C | C | C | C | T | T |
| 23 | | G | T | A | G | G | G | G | G | A | A |
| 24 | | T | C | G | T | C | C | C | T | G | G |
| 25 | SEC14L | T | T | C | | | | | T | T |

SEQUENCE LISTING

```
<160> NUMBER OF SEQ ID NOS: 186

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtcacccct gtgaaccgga                                                   20

<210> SEQ ID NO 2
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
ggtcaccagg tgacccagcc                                                     20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caaagtcaaa gagggcctgg acg                                                 23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttaggacct gtaaggatta a                                                   21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caaagtcaaa gagggcatgg acg                                                 23

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggggcgctcc accttattt                                                      19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggctgcgtc ctggctatct g                                                   21

<210> SEQ ID NO 8
<211> LENGTH: 24
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 8
cttcccgtcg tcactggtca tcat                                          24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtctgagca ctgctatggc                                               20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgcggtga tggaagttct c                                             21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaggtcaca gggctcttac ag                                            22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccactccta cagtgtggtc a                                             21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaatgttcca tagtacctga gg                                            22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gctctgtacc tgtacctctt atg                                               23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcagagaac attccaccag                                                   20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaagaacgc tcatcgtcct ct                                                22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtgtgccgag gaagtgaaga c                                                 21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catggcctcc aagcatccag                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgcctgtat aggtcagttc                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
ctcaatccat tctgctgcca                                               20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggactcata atacagcctt ac                                            22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcagtatcaa cgtggcaacc                                               20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttcggactgt caaccactga gag                                           23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctaggaccc gatgaggatt                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccaggaaagg ccagagcatc                                               20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 26
gtggccgtgg agaatcagaa cc                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgatagagc ctagacccac tg                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctgaaatgg agttacagtg ag                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtgagtttg atgctgaagt gc                                              22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcagctccct ggttctcatt c                                               21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tatgatccgc aggcttgtgt g                                               21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
```

```
acattcaaac ggtttctcgc ag                                           22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aggtcacggg acacctgctg t                                            21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtatctggac gagatcaagc ac                                           22

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaagcaccac atagtgtgg                                               19

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
actccaggag cttgcagcat gaa                                          23

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaaatcacg ctagggttca tc                                           22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```
gcactgtgac tttacatggc ac                                           22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtgctggtt tctcaggaca g                                            21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caggacgggt cacgtcttta g                                            21

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gttcctgtat gtcctagact tg                                           22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgcagacat ctgcctgtgt g                                            21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cagcacagac tgcattgctt c                                            21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgggacagaa agtgtcacct c                                            21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cacctagatt tcagattcct gg                                        22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
caagaggatt tgcctctatt agg                                       23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tttgcctcac cagttccagg                                           20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
aaacctgact tcccagaacc                                           20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tggaaactca cctggtctct g                                         21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
taggccatgt cctcttgctg c                                         21

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aacctctctg aaccttgatg ag                                    22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gtggctcagt cagttaggtg tc                                    22

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
ggtgaccggg tggctcagtc a                                     21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tcagaacctt cttgagtttg c                                     21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ggatatgggc tctagaatac c                                     21

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gaatagagct gggtactgta cc                                    22

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcctagatgg ctcagtcagt                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcagggtctc ttgtgaggct                                          20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tatatgccag acactcgctg g                                        21

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cagatctcag ttcaggatag ag                                       22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gagcaccctt cctttctcaa g                                        21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cagtgtgcga caggatgaca g                                        21

<210> SEQ ID NO 63

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggcatctggc ctgtcatcac t                                             21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgagttctga agaccctcct t                                             21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gacgagtcag ggattcttca                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tgaggtcacg cagcaggttc                                               20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acccgtaagc agagacagtt c                                             21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caccccagga gagtagaaat c                                             21

<210> SEQ ID NO 69
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tcactgcctg ccgagctgta g                                           21

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcagccaatg ctgaccagtg ct                                          22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cctggtgtga gtccgtcatt ac                                          22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aggaactcct ctcacacttt tg                                          22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccactcgata gttcacagat ac                                          22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cctgggactg tcattcctca g                                           21

<210> SEQ ID NO 75
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 75
tgggaatggg gtagacaaat                                                    20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aatgaagcca gaaagacaag g                                                  21

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gaccccttga caccgcttcc atct                                               24

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gccactgctg cccatcctga g                                                  21

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccagtggcag caggaacc                                                      18

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccgacctgct gcccacgact g                                                  21

<210> SEQ ID NO 81
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 81
ctcttcctac tcagcacctt g                                            21

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cccagactct gccttacctg                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcagcaggtc ggagagagac                                              20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggagcccaag ggcatcatgt g                                            21

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ctctcaactc tagtgagaca aag                                          23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cagggaggac tagtcattca ag                                           22

<210> SEQ ID NO 87
<211> LENGTH: 23
<212> TYPE: DNA
<213> ORGANISM: Artificial Sequence
<220> FEATURE:
```

<223> OTHER INFORMATION: Description of Artificial Sequence: Synthetic
     primer

<400> SEQUENCE: 87
caaaggtgaa atgatgagca ctg                                           23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 88
tcagctggaa tttgtgactg tg                                            22

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 89
ctgatttcct ggctgctcct accc                                          24

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 90
ttaactagct ggatgacatg gac                                           23

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 91
gaaatgccag ctgggatctg tg                                            22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 92
cttccctcag atgtggagtc ag                                            22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
ctgactccac atctgaggga ag                                            22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggaaggtgta aacacaatct gc                                            22

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctgttctagg gacctgctca g                                             21

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctctctcggc cctctctctc tg                                            22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acagctagtc ctttacctcc tc                                            22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccacctcatt agctctctgg tc                                            22

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 99
accccgccca tccgaact                                                  18

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
caggatgtcc tcgaggccca g                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
atgggaacat gaccagagag c                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcatatgtat cccacagaga g                                              21

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gatggtgcag ggctttaagg ag                                             22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggagatgcca ttgatgtgtg tg                                             22

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 105
gactgcagtg gtcttgttca g                                          21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ctcctgtgtc aatacctcct c                                          21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
actgttgcag cttctcaggt g                                          21

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgatttatgg aggactgact gtc                                        23

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctgtgacccg ttctttcaga g                                          21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tagagccccc taccttcaga c                                          21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aaatcatcct gtgtttcact g                                          21

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
catggatctg tattcactga cac                                        23

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
actcaagtgt cccagacctc g                                          21

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gggagttcag agctgtggag                                            20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gctcttctac taggtgtcct g                                          21

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cagagtctgg ttgttattcc tc                                         22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tctcaacatc gcgataactc tc					22

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccaccatctc gactttctca c					21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gtgaccagaa gtgagaaagt c					21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtgcgtccac gtgttcctaa g					21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
atggcagatt ctgtggaagt g					21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
agaccagact catggacact g					21

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gaatccggtc taccctgcta ag				22

```
<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gcattcagga tggtctcaag tag                                           23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cagtgccaca atcctgagat cag                                           23

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cacgactaca cagctacttg aa                                            22

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
agtaaaggtc actgtcagat ggcc                                          24

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cacgactaca cagctacttg aa                                            22

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tctggctggg gagtgtgttt g                                             21
```

```
<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggttcttgtc acttcacaca tc                                              22

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
agcactgaga caggacggtt g                                               21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gattcgtgac cacgtattga g                                               21

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gtccgagggg atgaagatgt ag                                              22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cccagttacc agaatactgc tc                                              22

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ccattaactc caccctgagc c                                               21
```

```
<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ggtgaagcca aagttccagt ag                                              22

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cctctggatg gccaggtcaa gtg                                             23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gttgattcct agggcttctg aag                                             23

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cgttcaacgg aacagacagt g                                               21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
aaaccagctt cccatctcct g                                               21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cacccaggac ctaacctctt g                                               21

<210> SEQ ID NO 142
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gaagtcctca caacagtatt atg                                           23

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gaagtgcagg tcactcacca g                                             21

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
caggagtcaa catgaaagat tc                                            22

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gctatgggag gtaaactcaa g                                             21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gtcaatttga agcgggttct g                                             21

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
aacctccaaa ttcgtagcca ag                                            22

<210> SEQ ID NO 148
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggtgtctacg gaacgtgtat tg                                              22

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cacagaggac cccactaact c                                               21

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gatctatgac agaggcatat ag                                              22

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ctgaggttcc ttccatgtct g                                               21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gactgccagg aagaagtggt g                                               21

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
caacatcaac tggatgtcat ac                                              22

<210> SEQ ID NO 154
<211> LENGTH: 22
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 154
catagcttta agatggaggc tg                                              22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gagatacttt catgactgcc ac                                              22

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggtaaggcac gtgtgtctta g                                               21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
aggtaggggt acagcaagtt c                                               21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cagaatgatc cagcccagat g                                               21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtgggtacct cctttggtgt g                                               21

<210> SEQ ID NO 160
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 160
acagggaaat tcacctaagt tgc                                              23

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gggttgcgta accatgacac a                                                21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gatcctcatc ctaggtaaga g                                                21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
atctattctg tgctgtcctg g                                                21

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ctcacactac agttacacat ac                                               22

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tgcaaactgt agattgcatc                                                  20

<210> SEQ ID NO 166
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 166
tcagtgtatg ccaagggttc ag                                            22

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gaaggcataa cattcgtgcc                                               20

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtaccataaa tacagcaaca tcc                                           23

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ccactacagg agagctgctt g                                             21

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
cctttactaa atgatgccag tac                                           23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gcactagtgt actgttaagt gtg                                           23

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 172
aagagcacac agccgtgctg ct                                              22

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tacctgatag gtcgaccgaa ga                                              22

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ctcgtggata gtacgtgtag t                                               21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tcactagaca gcacacttgc a                                               21

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tctgcagtgt tccagaaggt ag                                              22

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
agcatggcat tcttggattg gc                                              22

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 178
agtcagggca tggacagtag g                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ccttcaccag tgtccgctct g                                              21

<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cgatgccata cgtgcaaatc ac                                             22

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
atgtccacac agagcgcaca                                                20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tcagcagccg ctgttcctgc                                                20

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183 tggagctgc tcatggagaaa g                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 184
gaactcggcc ttctgctcaa g                                              21

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
agccagcaca aagcccccta cg                                             22

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcagcgctgg tacagttgaa ggat                                           24
```

METHOD FOR IDENTIFYING PROGRESSIVE ROD-CONE DEGENERATION IN DOGS

This application claims priority to U.S. application Ser. No. 60/750,433, filed Dec. 14, 2005, the disclosure of which is incorporated herein by reference.

FIELD OF THE INVENTION

The present invention relates generally to a canine disease termed progressive rod-cone degeneration ("prcd"). More particularly, the invention relates to DNA polymorphisms associated with progressive rod-cone degeneration in dogs.

DESCRIPTION OF RELATED ART

Progressive rod-cone degeneration (prcd) is an inherited canine retinal disease that occurs in multiple breeds of dog and closely resembles adult onset forms of autosomal recessive retinitis pigmentosa (RP). The disease initially was described as a form of Progressive Retinal Atrophy (PRA) affecting Miniature and Toy poodles (MP, TP). A resource colony of mixed breed dogs derived from such poodles was developed as a reference population, and used for mapping the disease locus to the centromeric end of canine chromosome 9 (CFA9) (Acland, 1998). This region on CFA9 is particularly gene rich, and exhibits suppressed recombination typical of centromeric chromosomal regions. The difficulty in proceeding from mapping data to causal gene identification, even with powerful experimental mapping pedigrees, is that the identified zero recombination region can still hold a daunting number of potential positional candidates.

A particularly opportune feature of this disease is that it occurs in multiple breeds of dog in which either allelic or identical mutations segregate. This was first demonstrated by crossbreeding experiments involving TP and MP, English and American cocker spaniels (ECS, ACS), and Labrador retriever (LR) breeds (Aguirre, 1988). This observation raised the possibility of using Linkage Disequilibrium (LD) mapping (Maniatis, 2002; Durrant, 2004) to further reduce the candidate gene region.

Dogs have been loosely divided into distinct breeds for at least hundreds of generations, and this division has intensified since the late 19th century with the development of "pure breed registries". Currently at least 400 breeds exist; each represents a genetic isolate with a defined and recorded history, has minimal gene flow with other breeds, and is derived from a rather small number of relatively recent founding ancestors (Vila, 1999; Wayne, 1999; Wilcox, 1995). Selective breeding practices further restrict the genetic diversity, increase founder effects, and increase the expected and observed extent of LD within breeds.

An initially reported zero recombination interval placed prcd between MYL4 and TK1, with no recombinations in 70 informative offsprings (Acland, 1998). Assuming conservation of synteny and order between the dog and human, this ~3.3 cM map interval corresponded to over 30 mb on HSA17q (HSA17: 42,641,426-73,681,775). Analysis of APOH, located between MYL4 and TK1 in HSA17, identified 3 recombinant dogs of 70 dogs examined, both excluding this gene as the prcd gene, and raising the possibility of micro-rearrangements in the prcd interval (Gu, 1999). Subsequently, a refined gene order map for the interval showed conservation of gene content between dog chromosome 9 (CFA9) and human chromosome 17 (HSA17q), and confirmed micro-rearrangements of gene order between the homologous regions (Sidjanin, 2003). A 1.5 mb physical map containing GRB2, a positional candidate gene within the zero recombination interval, placed it between FDXR and GALK1, and created a map with FDAR and SRP68 at the distal and proximal ends, respectively. However, there is an ongoing need to improve the physical map of CFA9 to identify a region having markers linked to the prcd disease for use in identifying dogs who are likely to be normal, carriers, or are affected with prcd.

SUMMARY OF THE INVENTION

The present invention provides a method for identifying dogs as likely to be genetically normal, carriers of, or affected with progressive rod-cone degeneration. The method comprises obtaining a biological sample comprising nucleic acids from a dog and analyzing the nucleic acid to identify whether the dog is likely to be normal, a carrier, or affected with prcd. Genetically normal dogs are considered those in which each chromosome 9 homolog does not exhibit polymorphisms that are part of the prcd disease haplotype. Affected dogs are considered those dogs in which each chromosome 9 homolog has the prcd disease haploptype. Carrier dogs are considered those where only one chromosome 9 homolog exhibits the prcd disease haplotype. Accordingly, representative polymorphisms of the prcd haplotype are also provided.

In one embodiment, the invention provides a method for identifying a normal dog by determining homozygosity for a wild type allele at a chromosomal location where prcd polymorphisms are found. In another embodiment, determining heterozygosity for any prcd polymorphism is indicative that the dog is likely not affected.

BRIEF DESCRIPTION OF THE FIGURES

FIG. 5 provides polymorphisms identified for the prcd region.

FIG. 6A provides a summary of ten animals sequenced to identify common haplotypes within the LD region. Two prcd-affected dogs and two prcd-heterozygous dogs contributed 6 disease-associated chromosomes representing 4 breeds. The LD region common to all affected chromosomes is highlighted in gray, and is estimated to be about 664 Kb.

FIG. 6B depicts subsequent fine scale mapping further reduced this LD interval to about 184 Kb (gray box)

DETAILED DESCRIPTION OF THE INVENTION

Figure 1:
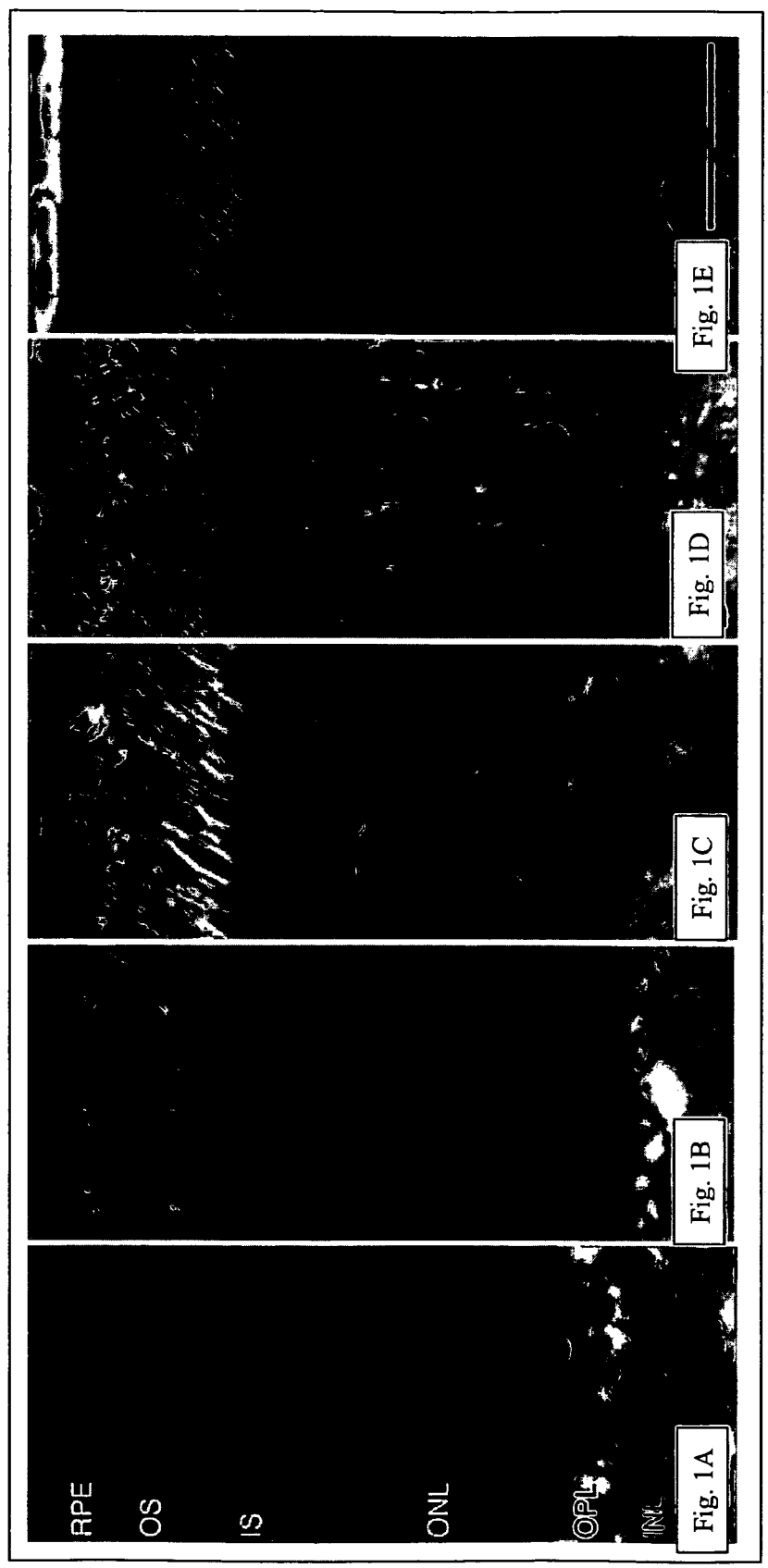
FIG. 1 provides a photographic representation of retinal micrographs showing non-allelism with prcd for the crosses between Basenji (A, 17.4 wk) or Italian greyhound (B, 17.4 wk) which were known to be affected with a form of PRA which was determined not be prcd and colony reference prcd-affected dogs; data for the Border collie cross is not illustrated. Retinal photoreceptors are normal. In contrast, crosses between the reference prcd-affected dogs and Australian cattle dog (C, 16.4 wk), Nova Scotia duck tolling retriever (D, 16.1 wk) and Portuguese water dog (E, 26 wk) show disorientation of the photoreceptor outer segments (OS) characteristic of the early stages of prcd. Calibration marker-25 μm; RPE=retinal pigment epithelium, IS=inner segment, ONL=outer nuclear layer, OPL=outer plexiform layer, INL=inner nuclear layer.

In the present invention, we have provided a revised physical map of CFA9 by creating a polymorphism map based upon the identification of single nucleotide polymorphisms (SNPs), as well as insertions and deletions (collectively "indels") on CFA9. Specifically, we have determined that a portion of CFA9 that comprises polymorphisms characteristic of the prcd haplotype lies in the region of canine chromosome 9 defined by nucleotide position 8,177,621 (represented by polymorphism #1 in GRB2 in FIG. 5) through 6,682,136 (represented by polymorphism #161 in SEC14L of FIG. 5.) This region is referred to herein as "the prcd region." Nucleotide positions as set forth in FIG. 5 are numbered in accordance with the dog (*Canis familiaris*) whole genome shotgun assembly, v2.0, which is publicly accessible at http://genome.ucsc.edu/cgi-bin/hgGateway and which is incorporated herein as of the May 2005 entry. "Wild type" alleles are considered those set forth in this assembly (as well as the nucleotide sequence that is complementary thereto). A polymorphism that is indicative of the presence of the prcd haplotype is referred to herein as a "prcd polymorphism."

We have also determined that the prcd region comprises a fine-scale affected haplotype, which includes, but is not limited to 98 polymorphisms, located within an 106 kb common LD region. This 106 kb region is bounded by SNP number 29 in FIG. 5 (CFA9 nucleotide number 7,217,488), and SNP number 128 (CFA9 nucleotide number 7,110,867 where the intervening LD region is highlighted in grey). This disease haplotype is present in all affected chromosomes within and among the multiple breeds of dog affected with prcd. However, we have also determined that other polymorphisms outside the common LD region, but within the prcd region, are also informative with respect to the prcd status of a dog and therefore are considered part of the prcd haplotype.

Accordingly, the present invention relates to a method for identifying dogs as likely to be genetically normal, carriers of, or affected with progressive rod-cone degeneration. Progressive rod-cone degeneration is also referred to herein as "prcd." Genetically normal dogs are those in which each chromosome 9 homolog of the dog lacks polymorphisms that are part of the prcd disease haplotype. Affected dogs are those in which each chromosome 9 homolog of the dog has the prcd disease haploptype. Carrier dogs are those in which only one chromosome 9 homolog of the dog exhibits the prcd haplotype.

The method of the invention comprises obtaining a biological sample from a dog and testing the biological sample to identify whether the dog likely to be normal, likely to be a carrier, or likely to be affected with prcd. "Normal" is considered to mean that the dog exhibits wild type alleles on both of its number 9 chromosomes at the locations where polymorphisms that constitute the prcd haplotype reside, examples of which are set forth in FIG. 5 under "SNP location." The term "SNP location" in this Figure refers to all types of prcd polymorphisms, including indels and repeats.

In one embodiment of the invention, a dog likely to be normal can be readily identified by determining homozygosity for a wild type allele at any chromosomal location where prcd polymorphisms are found (i.e., the absence of a prcd polymorphism on both chromosome 9 homologs at a particular location). In contrast, determining the presence of a prcd polymorphism is indicative that the dog is likely to be a carrier or affected, dependent upon whether the dog is heterozygous or homozygous for the particular prcd polymorphism investigated. As used herein, heterozygous for a prcd mutation means that one chromosome 9 homolog harbors a prcd polymorphism at a particular location, while the other homolog exhibits a wild type allele for the same location. Homozygous for a prcd polymorphism means that each chromosome 9 homolog has a prcd polymorphism at the same chromosomal location, meaning the same nucleotide position as in its homolog. Thus, in one embodiment of the invention, determining heterozygosity for any prcd polymorphism is indicative that the dog is likely not affected, since heterozygosity indicates the presence of one wild type normal (i.e., "normal") chromosome. Accordingly, in addition to the heterozygous condition for a prcd polymorphism being indicative that the dog is likely not affected, it is also considered indicative that the dog is likely a carrier of prcd. However, for determining whether a dog is likely normal, a carrier, or affected with prcd, it is preferable to determine the status of multiple prcd polymorphisms to decrease the probability of false identification of a normal or an affected chromosome, wherein an "affected chromosome" is a chromosome that comprises the prcd haplotype, and a normal chromosome is a chromosome that does not comprise the prcd haplotype. Accordingly, a preferred embodiment of the invention comprises determining the presence or absence of two prcd polymorphisms. In increasingly preferred embodiments, the presence or absence of three, four, five or six prcd polymorphisms may be determined. In this regard, it is considered that a finding of at least any six prcd polymorphisms will identify any dog as affected (or as a carrier) with prcd at a high confidence level. In order to confirm the results of any particular test, prcd status can be definitively established by analyzing a sample for the F04 mutation, which is the location of a prcd SNP that considered 100% predictive of the disease in all breeds. This SNP is listed as prcd polymorphism number 71 in FIG. 5.

Also provided is a method for selecting dogs for breeding, wherein dogs identified as likely to be carriers or likely to be affected can be removed from breeding stock. Alternatively, dogs identified as normal can be cleared for breeding.

In addition to representative prcd polymorphisms we have identified in the prcd region, FIG. 5 also provides primer sequences ("Primers") suitable for detecting prcd polymorphisms as designated by the "SNP location" column. The "BAC" column provides identification of the BAC clone(s) used to identify the listed prcd polymorphisms. The "Alleles" column depicts alleles observed in tested animals, while the "Affected alleles observed" indicates prcd polymorphisms that are indicative of an affected chromosome. For example, if an allele is "observed" but is not an "Affected observed allele", such as the "T" for SNP #5 in FIG. 5, a finding of a T at this location would provide information with a high confidence level that the chromosome on which the T allele is observed does not carry the prcd haplotype, i.e., that it is not a disease-carrying chromosome. If the T is homozygous then the animal is likely homozygous normal for the disease. If the T is heterozygous with the observed C allele, the animal is likely to be a carrier of prcd. Consistent with this, any prcd polymorphism presented in FIG. 5 is suitable for determining whether a dog is likely to be normal, a carrier, or affected with prcd. However, it will be recognized by those skilled in the art that certain prcd polymorphisms may be more informative, meaning their presence (or absence) provides a more certain prediction of the prcd status for certain breeds of dog. Thus, selection of a particular prcd polymorphism for analysis according to the method of the invention can be made by one skilled in the art in connection with the breed being tested. Additionally, it is preferable to determine the presence or absence of certain prcd polymorphisms, such as those listed in Table 1.

TABLE 1

| | Name | Location | Alleles | Affected allele |
|---|---|---|---|---|
| 1 | GRB2a | 8177621 | A/G | A/G (depending on the breed and with rare exception within breeds) |
| 2 | GRB2e | 8177229 | A/G | A/G (depending on the breed and with rare exception within breeds) |
| 3 | GRB2b | 8177123 | A/G | A/G (depending on the breed and with rare exception within breeds) |
| 4 | GRB2d | 8176052-060 | d1(no deletion)/d2 (9 bases deletion) | d1/d2 (depending on the breed and with rare exception within breeds) |
| 5 | AANAT | 7237330 | A/G | A (rarely G) |
| 6 | K9STS44p44 | 7217488 | A/G | A (rarely G) |

TABLE 1-continued

| | Name | Location | Alleles | Affected allele |
|---|---|---|---|---|
| 7 | K9STS48p48 | 7207443 | C/T | T |
| 8 | CYGB | 7198172 | A/G | A |
| 9 | CYGB31F5 | 7192970 | A/C | A |
| 10 | Poly3 | 7186710 | A/G | A |
| 11 | STHM-NaeI | 7164625 | T/C | T |
| 12 | STHM-AvaI | 7164570 | A/G | G |

Particularly preferred polymorphisms include SNPs 1, 2, 3, and 4 in GRB2, SNP 20 in AANAT, SNP 116 in ST6GalNac2 and SNP 161 in SEC14L (SNP locations refer to FIG. 5). While representative prcd polymorphisms are presented in FIG. 5 and Table 1, determination of additional polymorphisms in the prcd region are within the purview of one skilled in the art. In this regard, any of a variety of sequencing techniques and/or techniques for comparing nucleic acids known in the art can be used to identify additional polymorphisms suitable for use in the method of the invention. In general, such polymorphisms can be identified by comparing DNA sequences in the prcd region obtained from carrier and/or affected dogs and comparing those sequences with the corresponding normal sequence, wherein for the purposes of the present invention the normal sequence can be the *Canis familiaris* whole genome shotgun assembly noted above, or a sequence obtained from any dog known to be normal for prcd or sequences from a chromosome known to lack the prcd haplotype. By comparing sample sequences to a normal sequence, detection of polymorphisms which are linked to the prcd disease can be identified by those skilled in the art using standard population genetics and statistical analysis method.

For determining prcd polymorphisms in biological samples, the method of the invention can be carried out on any suitable biological sample obtained from a dog. In a preferred embodiment, the biological sample is any tissue containing genomic DNA. Suitable sources of biological samples include blood, hair, mucosal scrapings, semen, tissue biopsy, or saliva. In one embodiment, the biological sample is blood.

The method of the invention may be carried out by testing either DNA (or RNA in cases where the prcd polymorphism is present in an exon) isolated from a biological sample using a variety of techniques that are well known in the art. The DNA may be used directly or may be amplified enzymatically in vitro through use of PCR (Saiki et al. Science 239:487-491 (1988)) or other in vitro amplification methods such as the ligase chain reaction (LCR) (Wu and Wallace Genomics 4:560-569 (1989)), strand displacement amplification (SDA) (Walker et al. PNAS USA 89:392-396 (1992)), self-sustained sequence replication (3SR) (Fahy et al. PCR Methods Appl. 1:25-33 (1992)), prior to polymorphism analysis. The methodology for preparing nucleic acids in a form that is suitable for polymorphism detection is well known in the art.

Detection of prcd polymorphisms can be accomplished by a variety of methods including, but not limited to, restriction-fragment-length-polymorphism detection based on allele-specific restriction-endonuclease cleavage (Kan and Dozy Lancet ii:910-912 (1978)), hybridization with allele-specific oligonucleotide probes (Wallace et al. Nucl Acids Res 6:3543-3557 (1978)) including immobilized oligonucleotides (Saiki et al. PNAS USA 86:6230-6234 (1989)) or oligonucleotide arrays (Maskos and Southern Nucl Acids Res 21:2269-2270 (1993)), allele-specific PCR (Newton et al. Nucl Acids Res 17:2503-25 16 (1989)), mismatch-repair detection (MRD) (Faham and Cox Genome Res 5:474-482 (1995)), denaturing-gradient gel electrophoresis (DGGE)

(Fisher and Lerman et al. PNAS USA 80:1579-15106 (1983)), single-strand-conformation-polymorphism detection (Orita et al. Genomics 5:874-879 (1983)), RNAase cleavage at mismatched base-pairs (Myers et al. Science 230: 1242 (1985)), chemical (Cotton et al. PNAS USA 85:4397-4401 (1988)) or enzymatic (Youil et al. PNAS USA 92:87-91 (1995)) cleavage of heteroduplex DNA, methods based on allele specific primer extension (Syvanen et al. Genomics 8:684-692 (1990)), genetic bit analysis (GBA) (Nikiforov et al. Nuci Acids Res 22:4167-4175 (1994)), the oligonucleotide-ligation assay (OLA) (Landegren et al. Science 241: 1077 (1988)), the allele-specific ligation chain reaction (LCR) (Barrany PNAS USA 88:189-193 (1991)), gap-LCR (Abravaya et al. Nucl Acids Res 23:675-682 (1995)), and radioactive and/or fluorescent DNA sequencing using standard procedures well known in the art.

Further, several new techniques have been described including dynamic allele-specific hybridization (DASH), microplate array diagonal gel electrophoresis (MADGE), Pyrosequencing™, the TaqMan system as well as various DNA "chip" technologies such as the Affymetrix Polymorphism chips. These methods require amplification of the target genetic region, typically by PCR. Still other newly developed methods, which may not need PCR are based on the generation of small signal molecules by invasive cleavage followed by mass spectrometry or immobilized padlock probes and rolling-circle amplification. Several of the methods known in the art for detecting specific SNPs are described in U.S. Pat. No. 6,720,141, from which the description of the methods is incorporated herein by reference.

The representative prcd polymorphisms depicted in FIG. 5 were obtained in accordance with the following Example which is not intended to limit the present invention.

EXAMPLE 1

In order to identify the prcd region, polymorphisms and their linkage to the prcd disease were identified as set forth in this Example. Abbreviations utilized in this Example are as follows:

ACD=Australian cattle dog; ACS=American cocker spaniel; AE=American eskimo; BC=Border collie; CBR=Chesapeake Bay retriever; ECS=English cocker spaniel; IG=Italian greyhound; LR=Labrador retriever; MP=Miniature Poodle; NSDTR=Nova Scotia duck tolling retriever; PWD=Portuguese water dog; TP=Toy poodle.

Study Animals

Several different populations of dogs were used that included:

prcd reference colony: The prcd strain of dogs is maintained as part of an NIH-sponsored project (EY-06855) at the Retinal Disease Studies Facility (RDSF) in Kennett Square, Pa. This strain was derived from the original research colony of purebred MP in which the phenotype and inheritance of prcd were characterized [38]. Several prcd affected dogs were bred to homozygous normal unrelated MP, Beagles, and Beagle-crossbred dogs, and the heterozygous F1 progeny were then backcrossed to prcd-affected dogs to yield litters segregating the prcd phenotype. Nine related three-generation families from this colony with 70 prcd-informative progeny were studied [13]. Because the prcd reference colony was MP derived even though it is now highly outcrossed, we refer to them as MP. Additional independent lines derived from ACS and LR also are maintained separately.

Purebred and other dogs: Once allelism with prcd was established for ACD, NSDTR and PWD, a representative of each of these breeds was included for genotype analysis. In addition, selected privately owned dogs from breeds in which a form of retinal degeneration was segregating had DNA extracted from blood or tissue samples, and were typed for prcd-interval SNPs to test for association of markers with the disease (FIG. 5). Ten further dogs were selected for re-sequencing to develop the initial prcd-interval haplotype. These included prcd-affected (MP-NSDTR crossbred, ACD) and carrier (MP-Beagle crossbred, LR) dogs, and, in addition, dogs that were known not be affected with prcd (BC, English mastiff, Basenji, English springer spaniel, Glen of Imaal terrier, Papillon). In addition, samples from four Red Wolves (Canis rufus) were similarly tested. Selected samples from a subset of the above dogs (MP-NSDTR crossbred, ACD, Basenji) plus additional samples from a prcd-affected CBR and a PWD were further re-sequenced to define the final fine scale haplotype map for the prcd interval.

Identification of prcd in New Isolate Populations

We selected 6 different breeds of dogs whose clinical retinal degeneration was clinically similar to prcd, and confirmed the disease in 3 of them. The breeds used for the allelism study included ACD, NSDTR, PWD, Basenji, IG and BC. Affected dogs from these breeds were mated to prcd-affected mix-breed colony dogs derived from MP or ECS lines. All dogs resulting from these matings were euthanatized with a barbiturate overdose after 14 weeks of age, and the retinas fixed and embedded in plastic for high-resolution optical microscopy [15].

Ascertainment of prcd Status

Diagnosis of prcd was based on a combination of clinical examination, including indirect ophthahnoscopy and electroretinography, and retinal morphology using a combination of previously published ascertainment criteria for the disease [13; 15; 39]. For morphologic studies, hallmark retinal photoreceptor abnormalities are visible in animals 14 weeks of age and older using high-resolution optical microscopy [15; 38].

Blood Collection and DNA Extraction

DNA was extracted from whole blood samples collected from dogs with either citrate or EDTA using a standard phenol-chloroform-based purification protocol. In some cases the DNA was purified using Qiagen Mini Blood DNA kit (Qiagen, Valencia, Calif.) according to the manufacturer's protocol.

BAC Library Screening, Sequencing and Analysis

The physical map of the prcd interval [16] was extended to cover regions that include AANAT and SEC14L, two genes within the candidate region. The BAC library was probed with canine AANAT and SEC14L cDNA probes, and positive BACs were identified and purified according to standard techniques and as previously described [16]. BAC ends were sequenced, and BAC end-STSs were used to extend the BAC contig, and establish the minimal tiling pass. 3.2X sequence was generated for those BACs, and analyzed as previously described [16], and the order of the genes within that interval established.

Primer Design, PCR Amplification and Sequencing

Primers were designed from the 3.2X consensus sequence of specific BAC clones for standardized amplification conditions selected for a Tm between 56° C. and 63° C., and minimal risk of primer-dimer formation. 20 ng of DNA were mixed with 1×PCR reaction Buffer (Invitrogen, Carlsbad, Calif.), 1.5 mM MgCl2, 0.2 mM dNTPs, 200 µM forward and reverse primers, and 1 unit of Taq DNA polymerase (Invitrogen) in a final volume of 25 µl. The DNA was then denatured at 96° C. for 3 minutes, and 35 cycles of 94° C. for 30 seconds, 55° C. for 30 seconds and 72° C. for 1 minute/1000 bp were performed in a thermal cycler (MJ Research, Watertown, Mass.). An additional final extension time of 5 minutes at 72° C. insured full length products. When necessary, PCR reactions were optimized by increasing the annealing temperature to 58° C. or 60° C. For GC-rich amplicons, the Failsafe kit (Epicentre, Madison, Wis.) was used following the manufacturer's protocol. PCR products were run on 1.8% agarose, and stained with ethidium bromide (2 µg/ml in a water bath). Single specific PCR products were extracted using the Qiagen PCR extraction kit (Qiagen), and eluted in 10 mM Tris-HCl (pH=7.5). If more than one amplification product was detected, the specific product was extracted from the gel using a Qiagen Gel extraction kit (Qiagen). 200 ng/1000 bp PCR product was mixed with 8 pmole of either forward or reverse primer and DNA sequencing was performed using the Applied Biosystems Automated 3730 DNA Analyzer (Applied Biosystems, Foster City, Calif.). Each PCR product was sequenced with the forward and reverse primers. Sequences were then analyzed and compared using Sequencher® 4.2.2 Software (Gene Codes Corporation, Ann Arbor, Mich.).

GRB2 Haplotypes

A GRB2 allele is composed of 4 polymorphisms that create a haplotype (FIG. 5, polymorphisms number 1 to 4; amplicon IDs a, e, b and d). The different alleles are: H1=[A-G-G-no deletion]; H2=[G-A-A-no deletion]; H3=[A-G-G-9 bases deleted]; H4=[G-G-A- no deletion]

Northern Analysis

10 µg of total RNA was mixed with 10 µg/ml ethidium bromide and 3× of gel loading buffer (Ambion, Austin. Tex.) in a final volume of 10 µl, heated at 65° C. for 10 minutes, chilled on ice for 2-3 minutes and loaded on a 1% agarose-formaldehyde denaturing gel; 31 g of 0.24-9.5 kb RNA ladder was used as a size marker (Invitrogen, Carlbad, Calif.). The gel ran with continuously circulating 1×MOPS running buffer (Ambion) for 16 hours at 21 volts. After three 5 min washes in DEPC treated water, 20 min in 0.05N NaOH, and a 15 min soak in 10×SSC, transfer to a nylon-based membrane (GeneScreen Plus, NEN Life Science, Boston, Mass.) was done with 10×SSC buffer using a standard protocol. Full transfer was confirmed by exposing the gel to UV light. The membrane was washed in 2×SSC for 2 min, and RNA was cross-linked to the membrane (exposure=0.12 joules per cm$^2$; Stratalinker UV Crosslinker, Stratagene, La Jolla, Calif.). Northern probes were amplified from cDNA clones containing the respective genes (Accession DQ336162-DQ336165) with gene specific primers.

```
RHBDL6:
F:  CCTTCACCAGTGTCCGCTCTG;        (SEQ ID NO:179)
R:  CGATGCCATACGTGCAAATCAC         (SEQ ID NO:180)

AANAT:
F:  ATGTCCACACAGAGCGCACA;          (SEQ ID NO:181)
R:  TCAGCAGCCGCTGTTCCTGC;          (SEQ ID NO:182)

CYGB:
F:  TGGAGCTGCTCATGGAGAAAG;         (SEQ ID NO:183)
R:  GAACTCGGCCTTCTGCTCAAG;         (SEQ ID NO:184)

ST6GalNac2:
F:  AGCCAGCACAAAGCCCCCTACG;        (SEQ ID NO:185)
R:  TCAGCGCTGGTACAGTTGAAGGAT.      (SEQ ID NO:186)
```

Probes were labeled with alpha-dCTP-P$^{32}$ using RadPrime DNA labeling System (Invitrogen), and pre-hybridization (68° C. for 30 minutes) and hybridization were carried out with ExpressHyb solution (Clontech, Mountain View, Calif.). The labeled probe was denatured at 95° C. for 5 minutes, chilled on ice, and added to a fresh pre-warm ExpressHyb solution. The ExpressHyb solution was replaced with the fresh solution containing the radiolabeled cDNA probe. Hybridization was carried out at 68° C. for 16-18 hours, blots rinsed several times with 2×SSC, 0.05% SDS; the washes with the same solution were done twice with continuous agitation for 40 min. Then the blot was washed with 0.1×SSC and 0.1% SDS with continuous shaking at 50° C. for 40 min with one change of fresh solution. Blots were exposed to x-ray film at −70° C. for 24-96 hours with two intensifying screens. Loading control was achieved by hybridizing canine specific mactin (Z70044) probe to the membranes under the same conditions, and exposure to x-ray film for 4 hours.

Phylogenetic Analysis of prcd Chromosomes

Individual chromosomes were assigned to the respective breed and transmittal of the affected phenotype according to pedigree information. Genetic distance between chromosomes was calculated from SNP data based on the Kimura 2-parameter with a transition/transversion ratio=2.0 [40; 41], and clustered under the neighbor-joining method [42] using the PHYLIP package [43; 44]. Confidence in the resulting branches was inferred by 100 bootstrap [45]; the consensus cluster was chosen based on the extended majority rule. The 79 SNP's used for analysis come from FIGS. 5 (SNPs 30, 56, 65, 83, 88, 95, 98 and 116), 2A (46 SNPs and 3 GRB2 polymorphisms) and 2B (22 SNPs).

Results

Interbreed Crosses Identify New prcd Breeds

To identify additional independent populations with prcd for use in the LD studies, a series of interbreed crosses were carried out using prcd-affected dogs from the reference colony. When bred to Basenji, Border collie (BC), or Italian greyhound (IG) dogs affected with retinal degeneration, all resultant progeny had morphologically normal retinas, thus excluding allelism with prcd (FIG. 1, A, B). In contrast, a similar strategy used with retinal degenerate Australian cattle dog (ACD), Nova Scotia duck tolling retriever (NSDTR), or Portuguese water dog (PWD) demonstrated that all the progeny were affected. In these 3 breeds, the retinas showed mild disorganization and disorientation of the photoreceptor outer segments, the hallmark early lesions of prcd (FIG. 1, C-E) [15], and confirmed allelism with prcd.

Tiling Path of the prcd Interval

Figure 2:
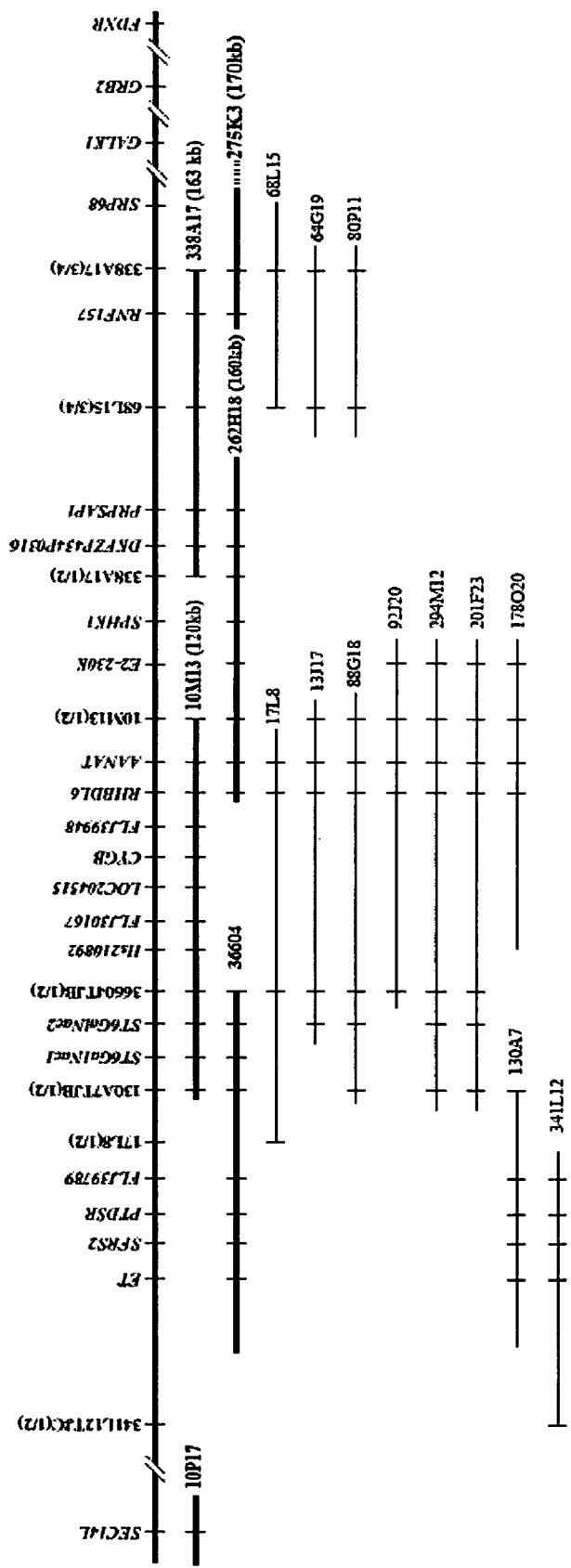
FIG. 2 provides a schematic representation of the prcd LD interval. Low-pass 3.2X sequence of ~1.2 Mb from 6 BAC clones from the candidate region was analyzed. Ten affected haplotypes observed in different breeds are illustrated which reduced the LD to ~106 Kb. Haplotypes 1-4 are common haplotypes found in specific affected breeds: Haplotype 1 in MP, TP, ECS, ACS, LR, PWD and CBR; Haplotype 2 in NSDTR; Haplotype 3 in ACD; Haplotype 4 in AE. Haplotypes 5-10 represent rare recombinant chromosomes observed in ACS(H5), NSDTR (H6), PWD (H7), LR (H8), MP and TP (H9) and TP (H10). Representative SNPs and indels show heterozygosity between the affected chromosomes. The final LD is boxed and contains 98 polymorphisms shared among all affected chromosome, and is represented here by 6 SNPs. Distances and recombination points are not drawn to scale. The 4 markers described in Table 2 (GRB2, AANAT, ST6GalNac2, SEC14L) are in bold letters. For the full data set see FIG. 6. Large black dots in Haplotypes 1 and 2 represent nucleotide deletions.

The previously published physical map [16] was extended with overlapping BAC clones 275K3, 33817, 262H18, 10M13, 36604; a sixth BAC, 10P17, that contained SEC14L but did not overlap the tiling path, was also included for analysis (FIG. 2). To facilitate identification of SNPs for LD map construction, primers were designed from the 3.2×BAC sequence to amplify regions that did not include repetitive elements, and new markers were developed.

Broad Scale Analysis of the GRB2-SEC14L Candidate Region

Linkage analysis in the reference population placed prcd in a zero recombination interval between GRB2-SEC14L, a distance estimated at 1.5 Mb and which constitutes the prcd region (FIG. 2). This region contains at least 40 known and hypothetical genes (May 2005 dog (Canis familiaris) whole genome shotgun (WGS) assembly v2.0; http://genome.ucsc.edu/cgi-bin/hgGateway). Four genes (GRB2, AANAT, ST6GalNac2 and SEC14L) were evaluated to set limits for developing an LD map. Polymorphisms were identified in the 4 genes (FIG. 5: SNPs 1, 2, 3, and 4 in GRB2, SNP 20 in AANAT, SNP 116 in ST6GalNac2 and SNP 161 in SEC14L), and these co-segregated with the disease in the 70 informative colony dogs with no recombinants. Typing the 4 markers for >100 dogs/breed, both affected and unaffected relatives, was used to establish that different prcd-associated haplotypes segregated in the 10 different breeds or breed varieties (Table 2A; MP/TP, ECS, ACS, NSDTR, PWD, ACD, LR, Chesapeake Bay retriever (CBR) and American eskimo (AE)).

TABLE 2

| Breed | GRB2 allele | AANAT allele | ST6GalNac2 allele | SEC14L allele |
|---|---|---|---|---|
| A Common breed-specific haplotypes observed in homozygous state in affected dogs | | | | |
| Poodles (Miniature and Toy) | H1 | A | A | A |
| English cocker spaniel | H1 | A | A | A |
| American cocker spaniel | H1 | A | A | A |
| Labrador retriever | H1 | A | A | A |
| Portuguese water dog | H1 | A | A | A |
| Chesapeake Bay retriever | H1 | A | A | A |
| Nova Scotia duck tolling retriever | H2 | A | A | G |
| Australian cattle dog | H2 | A | A | G |
| American eskimo | H3 | A | A | A |
| B. Rare haplotypes observed in affected dogs | | | | |
| Portuguese water dog (n = 2) | H3 | A | A | A |
| Nova Scotia duck tolling retriever (n = 1) | H4 | A | A | G |
| American cocker spaniel (n = 1) | H4 | A | A | A |
| Labrador retriever-German origin (n = 2) | H2 | A | A | A |
| Labrador retriever (n = 2) | H3 | A | A | A |
| Toy poodle (n = 2) | H2 | G | A | A |
| Miniature poodle (n = 2) | H2 | G | A | A |
| Chesapeake Bay retriever (n = 2) | H1 | A | A | G |
| Portuguese water dog (n = 1) | H1 | A | A | G |
| Toy poodle (n = 1) | H1 | A | A | G |
| Australian Cattle Dogs (n = 1) | H2 | A | A | A |

The haplotypes were different at the GRB2, AANAT and SEC14L loci, while the ST6GalNac2 "A" allele was the same in all haplotypes. At the GRB2 locus, 4 non-redundant polymorphisms defined 4 alleles, H1, H2, H3 and H4, that cosegregated with prcd in different populations (Table 2, FIG. 2). H1 was the most common GRB2 allele on prcd-affected chromosomes, cosegregating in 7 breed/breed varieties (MP/TP, ECS, ACS, LR, CBR, PWD). H2 was associated with the affected chromosome in NSDTR, ACD, and small subsets of LR, TP and MP (Table 2B). H3 cosegregated with prcd in the AE, and in a subset of LR and PWD. H4 was only observed in the heterozygous state in 1 prcd-affected dog each of the ACS and NSDTR breeds (Table 2B).

At the SEC14L locus, the "G" allele was in phase with prcd in NSDTR and ACD, and the "A" allele in the remaining 8 breeds/breed varieties (Table 2A). Five affected dogs (2 CBR, 1 TP, 1 PWD and 1 ACD) were exceptions, with heterozygous status (A/G) for this allele (Table 2B). At AANAT, the "A" allele initially was in phase with all affected animals tested (see below). The finding of 8 different haplotypes in the affected population using a limited number of polymorphisms for broad-scale characterization of the ~1.5 Mb interval (Table 2A, B) strongly suggested that the candidate region is within the interval flanked by GRB2 and SEC14L. Also, because of interbreed specificity in the haplotypes, it appeared that this region could be reduced further by LD analysis of different breeds. Nonetheless, these results demonstrate that polymorphisms outside the 106 kb region bounded by SNP number 29 in FIG. 5 and SNP number 128, but within the prcd region as defined herein, are suitable for determining the prcd status of a dog. A specific illustration of this is provided in Table 3. Table 3 provides a statistical characterization of one prcd polymorphism from Table 2 (AANAT) that lies outside the LD and which is useful in the method of the invention. The GG/GA/AA at "F04" represent Normal, Carrier & Affected, respectively. As noted above, F04 is the location of a prcd SNP that is 100% predictive of the disease in all breeds and is listed as prcd polymorphism number 71 in FIG. 5. As can be seen from Table 3, AANAT ranges between 69% to 100% predictive for prcd, depending on the breed.

TABLE 3

| Breed | GG at AANAT & GG @ F04 | GG at AANAT NOT GG @ F04 | GA at AANAT & GA @ F04 | GA at AANAT NOT GA @ F04 | AA at AANAT & AA @ F04 | AA at AANAT NOT AA @ F04 | # mismatches | Total tested | % error in genotype |
|---|---|---|---|---|---|---|---|---|---|
| ACD | 108 | 0 | 142 | 8 | 43 | 2 | 10 | 303 | 3% |
| ASTCD | 18 | 0 | 13 | 1 | 8 | 1 | 2 | 41 | 5% |
| CBR | 46 | 0 | 30 | 2 | 1 | 0 | 2 | 77 | 3% |
| ECS | 199 | 0 | 173 | 0 | 36 | 0 | 0 | 408 | 0% |
| LR | 634 | 0 | 654 | 583 | 88 | 65 | 648 | 2064 | 31% |
| NSDTR | 113 | 0 | 113 | 1 | 13 | 0 | 1 | 240 | 0% |

TABLE 3-continued

| Breed | GG at AANAT & GG @ FO4 | GG at AANAT NOT GG @ FO4 | GA at AANAT & GA @ FO4 | GA at AANAT NOT GA @ FO4 | AA at AANAT & AA @ FO4 | AA at AANAT NOT AA @ FO4 | # mismatches | Total tested | % error in genotype |
|---|---|---|---|---|---|---|---|---|---|
| Poodles | 765 | 2 | 273 | 42 | 44 | 10 | 54 | 1136 | 5% |
| PWD | 173 | 0 | 107 | 0 | 7 | 0 | 0 | 287 | 0% |
| Combined all breed Total | | | | | | | 717 | 4556 | 16% |

Fine-Scale Mapping of the LD Interval

We proceeded to construct a fine-scale haplotype of the LD interval. To do this, three regions of the physical map were chosen for initial screening in 10 dogs from different breeds (FIG. 2 and FIG. 6) Two prcd-affected (MP-NSDTR crossbred and ACD), and two carriers (MP-Beagle crossbred and LR) contributed 6 disease-associated chromosomes from 4 breeds. Six additional dogs from other breeds without prcd were used: BC, Basenji, English springer spaniel, Glen of Imaal terrier, English mastiff and Papillon. Together with the 2 normal chromosomes from the prcd carriers, a total of 14 normal chromosomes were examined from 8 different breeds. The screening of 20 chromosomes from 11 different breeds identified 47 SNPs; 23 of them (FIG. 6: SNPs 11 to 33) create a haplotype common to all affected chromosomes. Centromeric and telomeric to this region, the affected chromosomes from MP, ACD and NSDTR differ from each other, but the affected chromosomes of LR and MP are similar. Assuming the one founder hypothesis, this haplotype reduced the LD region for the tested breeds to approximately 664 Kb, and spanned 4 BACs (338A17, 262H18, 10M13 and 36604), and the region between BACs 36604 and 10P17 which was not characterized or sequenced.

Further reduction of the LD region was sought by fine-scale analysis of the 664 Kb interval. The physical map locates BAC 10M13 in the middle of the candidate region; analysis of SNPs from flanking regions of normal (BC) and several prcd-affected chromosomes from different breeds (MP-NSDTR crossbred, ACD, CBR, PWD) was carried out. The purebred prcd-affected CBR and PWD were chosen because they were recombinant at SEC14L, an indication that they might be informative for recombinations closer to the disease locus. Twenty-five additional polymorphisms, 22 SNPs, 2 indels and 1 microsatellite, were identified, and heterozygosity was observed between affected chromosomes in the distal and proximal ends (FIG. 2, Haplotypes 1, 2 and 3, and FIG. 6B). This identifies a haplotype common to all affected chromosomes that spans an ~184 Kb interval located between AANAT and ST6GalNac2. Outside of this interval, the NSDTR affected chromosome carried a different telomeric haplotype (FIG. 2, Haplotype 2) compared with the MP (FIG. 2, Haplotype 1), and the ACD (FIG. 2, Haplotype 3) differed from both of those 2 breeds. The PWD and the CBR, for the most part, have the same haplotype as the MP.

A further reduction of the LD region was accomplished after 4 poodles, two closely related TP and two unrelated MP, were found to be affected with a retinal degeneration clinically compatible with prcd, but with a different genotype at AANAT. Two were homozygous G/G, and two were heterozygous A/G. The dogs were then typed for the SNPs within the LD interval, and were found to have the affected haplotype centromeric to AANAT (Table 2B, FIG. 2, Haplotype 9). This historic recombination excludes AANAT from the LD region, and reduced the LD interval to 106 Kb. Nonetheless, we have determined that AANAT is an informative prcd polymorphism that is useful in the method of the invention as further set forth in Table 3.

Once the LD region was defined, a single fine-scale haplotype of the 106 Kb interval was assembled comprising 98 polymorphisms, and these were common to all prcd-affected chromosomes regardless of the breed (FIG. 5). From this haplotype, a subset of 7 SNPs was used to test an additional 10 breeds of dogs with inherited retinal degeneration that was clinically compatible with prcd. Four additional breeds, Entlebucher mountain dog, Chinese crested, Silky terrier and Finnish Lapphund, were found to share the same haplotype for the screening SNP subset. This brings the number of breeds/breed varieties that share this common haplotype to 14.

Evaluation and Exclusion of Positional Candidate Genes

Figure 3:
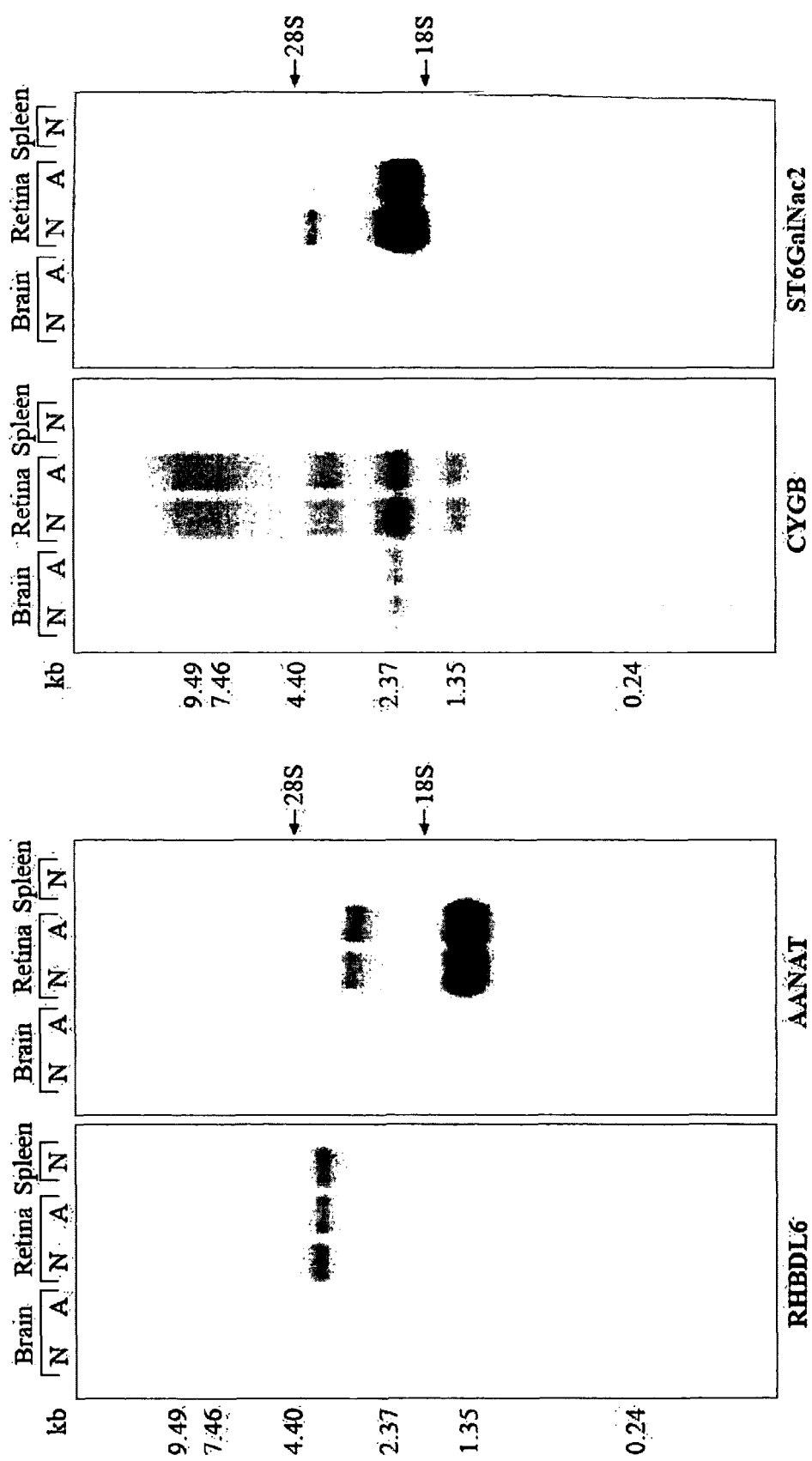
FIG. 3 is a photographic representation of RNA expression of positional candidate genes (RHBDL6, CYGB, ST6GalNac2, AANAT) in the dog. Expression profile is shown for normal (N) and affected (A) brain and retina, and normal spleen. No difference in expression is observed between affected, and non-affected brain and retina. RHBDL6 shows equal expression in retina and spleen. AANAT and ST6GalNac2 are not expressed in brain or spleen, but are highly expressed in the retina, and have two variants: ~1.3 kb (major transcript) and ~3.0 kb for AANAT, and ~2.2 kb (major transcript) and ~4.0 kb for ST6GalNac2. CYGB is expressed in brain and retina, but not in spleen, and shows 4 different transcripts. Ribosomal RNA is indicated as 28S and 18S, and β-actin was used as a loading control.

Prior to identifying ancestral recombinations between AANAT and the disease that reduced the LD interval to 106 Kb, we evaluated the 4 positional candidate genes in the 184 Kb candidate region: AANAT, RHBDL6, CYGB and ST6GalNac2. These were cloned (accession numbers: DQ336162, DQ336163, DQ336161, DQ336164), sequenced, and their retinal expression investigated. No differences were observed in retinal expression for the four genes (FIG. 3). In addition, only one sequence variant was identified; this was the G616A transition in AANAT. The exclusion of the AANAT SNP from causal association with prcd also was confirmed in studies that bred a BC derived crossbred and a purebred LR, each A/G for the G616A transition in AANAT, to A/A prcd-affected dogs from the reference colony (data not shown). However, the exclusion of AANAT from causal association with prcd disease means that the affected gene does not encompass AANAT, but AANAT is nonetheless an informative polymorphism. All A/A genotyped offspring had normal retinal structure when examined after the age of diagnosis. Together with the recombination results, the data confirm that the AANAT SNP is not the mutation, but rather a tightly linked benign polymorphism.

We continued examination of this interval and analyzed predicted exons of putative genes identified using a complementary EST project to characterize the canine retinome [17]. A G to A transition in codon 2 of a novel retinal expressed gene, provisionally termed PRCD, has been identified which changes the second amino acid from cysteine to tyrosine. The sequence change is present in all affected dogs from the different breeds/breed varieties with prcd. Identification of this G to A transition is indicative of an affected chromosome 100% of the time. This sequence change is provided as prcd polymorphism number 71 in FIG. 5.

Phylogenetic Analysis of prcd Chromosomes

Figure 4:
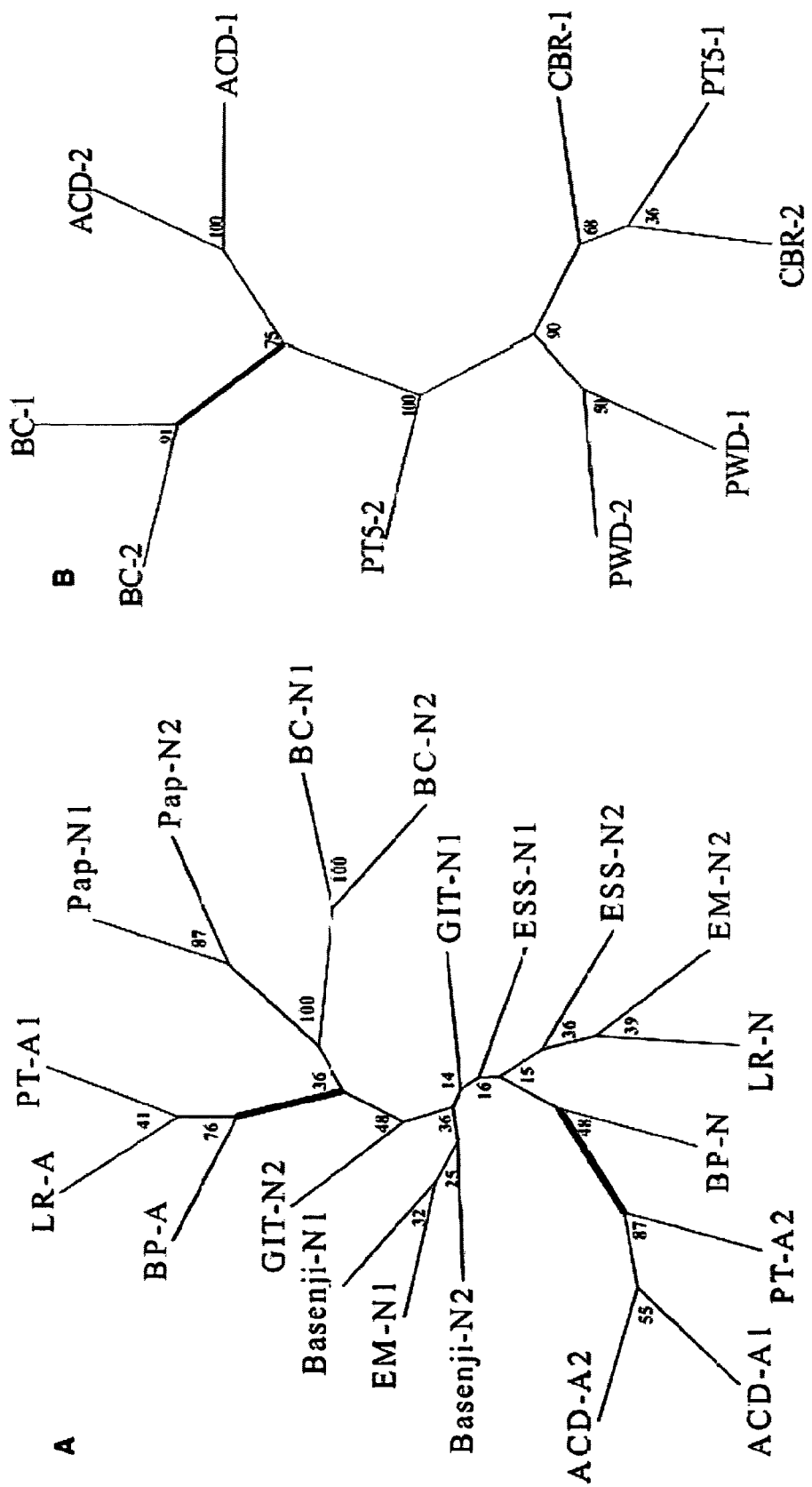
FIG. 4 is a graphical depiction of a bootstrapped neighbor joining cladogram representative of a genetic distance analysis between nine affected chromosomes (both chromosomes from affected ACD, PWD and CBR; single affected chromosomes from and Poodle-NSDTR crossbred and a heterozygous LR). Distances were calculated from 79 SNPs from the prcd candidate region (see Methods). Distances were calculated and clustered using the neighbor-joining method. Confidence in branching is inferred by bootstrap values (B=100). The individual haplotypes separate in one main cluster represented by Poodle, CBR and PWD. Affected chromosomes segregating in the NSDTR and ACD are clearly separated. Note that the PWD and CBR were selected because one chromosome from each was recombinant at SEC14L; the remainder of the haplotype was identical in both. NSDTR=Nova Scotia duck tolling retriever; ACD=Australian cattle dog; PWD=Portuguese water dog; CBR=Chesapeake Bay retriever.

The genetic distance was calculated for nine affected chromosomes using 79 SNPs and visualized as a bootstrapped neighbor joining cladogram (FIG. 4). Both affected chromosomes present in the ACD are completely separated from the cluster combining chromosomes derived from PWD, CBR, Poodle and LR, while the chromosomes observed in the NSDTR remains isolated from either cluster at this level. The distinction of these clusters becomes more apparent when compared to normal chromosomes, in which case the NSDTR clusters more closely with the ACD than the other breeds (data not shown). Thus, and without intending to be bound by any particular theory, it is considered that the affected chromosomes observed in the Poodles, LR, CBR and PWD separated more recently than the chromosomes derived from NSDTR and ACD, which are historically more isolated breeds.

Thus, in the present invention we have demonstrated that for prcd-affected chromosomes the prcd region extends over ~1.5 Mb distance, from GRB2 to SEC14L.

The invention has been described through specific embodiments. However, routine modifications to the compositions, methods and devices will be apparent to those skilled in the art and such modifications are intended to be covered within the scope of the invention.

REFERENCES

[1] N. Maniatis, et al. Proc Natl Acad Sci USA 99 (2002) 2228-33.
[2] C. Durrant, et al. Am J Hum Genet 75 (2004) 35-43.
[3] A. de la Chapelle, et al. Proc Natl Acad Sci USA 95 (1998) 12416-23.
[4] L. Peltonen, Hum Hered 50 (2000) 66-75.
[5] T. Varilo, et al. Hum Mol Genet 12 (2003) 51-9.
[6] V. C. Sheffield, et al. Trends Genet 14 (1998) 391-6.
[7] L. Kruglyak, Proc. Natl. Acad. Sci. USA 96 (1999) 1170-1172.
[8] D. Altshuler, et al. Nature 437 (2005) 1299-320.
[9] H. G. Parker, et al. Science 304 (2004) 1160-1164.
[10] N. B. Sutter, et al. Genome Res 14 (2004) 2388-96.
[11] N. B. Sutter, a et al. Nat Rev Genet 5 (2004) 900-10.
[12] G. D. Aguirre, et al., The Dog and Its Genome, Cold Spring Harbor Laboratory Press, Cold Spring Harbor, N.Y., 2006, pp. 291-325.
[13] G. M. Acland, et al., Proceedings National Academy of Sciences, USA 95 (1998) 3048-53.
[14] D. Serre, R et al., Genome Res 15 (2005) 1547-52.
[15] G. D. Aguirre, et al., Exp Eye Res 46 (1988) 663-87.
[16] D. J. Sidjanin, et al., Genomics 81 (2003) 138-48.
[17] B. Zangerl, et al., Invest Ophthalmol Vis Sci 47 (2006) 2632-2638.
[19] H. H. Kazazian, et al., Am J Hum Genet 35 (1983) 1028-33.
[20] N. Arrheim, C. et al., Proc Natl Acad Sci USA 82 (1985) 6970-4.
[21] R. J. Klein, et al., Science 308 (2005) 385-389.
[22] J. L. Haines, et al., Science 308 (2005) 419-421.
[23] A. O. Edwards, et al., Science 308 (2005) 421-424.
[24] J. R. Kidd, et al., Am J Hum Genet 66 (2000) 1882-99.
[25] K. A. Goddard, et al., Am J Hum Genet 66 (2000) 216-34.
[26] K. K. Kidd, et al., J Hered 95 (2004) 406-20.
[27] L. B. Jorde, et al., Hum Hered 50 (2000) 57-65.
[28] S. L. Sawyer, et al., Eur J Hum Genet 13 (2005) 677-86.
[29] D. M. Evans, a et al., Am J Hum Genet 76 (2005) 681-7.
[30] F. M. De La Vega, et al., Genome Res 15 (2005) 454-62.
[31] K. Lindblad-Toh, et al., Nature 438 (2005) 803-819.
[32] A. V. Smith, D et al., Genome Res 15 (2005) 1519-34.
[33] M. W. Neff, et al., Proc Natl Acad Sci USA 101 (2004) 11725-30.
[34] J. K. Lowe, et al., Genomics 82 (2003) 86-95.
[35] B. van de Sluis, et al., J Hered 94 (2003) 256-9.
[36] B. van De Sluis, et al., Hum Mol Genet 11 (2002) 165-73.
[37] T. J. Jónasdóttir, et al., PNAS 97 (2000) 4132-4137.
[38] G. Aguirre, et al., Invest Ophthalmol Vis Sci 23 (1982) 610-30.
[39] G. Aguirre, et al., Invest Ophthalmol Vis Sci 27 (1986) 635-55.
[40] M. Kimura, A et al., J Mol Evol 16 (1980) 111-20.
[41] L. Jin, a et al., Mol Biol Evol 7 (1990) 82-102.
[42] N. Saitou, et al., Mol Biol Evol 4 (1987) 406-25.
[43] J. Felsenstein, PHYLIP—Phylogeny Inference Package (Version 3.2). Cladistics 5 (1989) 164-166.
[44] J. Felsenstein, PHYLIP (Phylogeny Inference Package) version 3.5c. Distributed by the author, Department of Genetics, University of Washington, Seattle, 1993.
[45] J. Felsenstein, Evolution 39 (1985) 783-791.

We claim:

1. A method for identifying a dog as likely not to be affected with progressive rod cone degeneration comprising:
   a) obtaining a biological sample comprising nucleic acids from the dog; and
   b) testing the biological sample comprising the nucleic acids for the presence of at least one prcd polymorphism present on a chromosome 9 homolog; wherein the at least one prcd polymorphism is A, or T as the reverse complement of A, wherein the A or the T are located at nucleotide position 7217488 of canine chromosome 9 in the May 2005 *Canis familiaris* whole genome shotgun assembly, and wherein
   the presence of the at least one prcd polymorphism on only one chromosome 9 homolog or the absence of the at least one prcd polymorphism in both chromosome 9 homologs identifies the dog as likely to be not affected with progressive rod cone degeneration.

2. The method of claim 1, wherein the testing is carried out by amplifying the nucleic acids from the biological sample and determining the sequence of the amplified nucleic acids.

3. The method of claim 1, wherein the amplification is carried out by polymerase chain reaction.

4. The method of claim 3, wherein the nucleic acids are amplified by the polymerase chain reaction using primers selected from the group of primers defined in SEQ ID NO: 45 and 46.

5. The method of claim 1, wherein the biological sample is selected from the group consisting of blood, hair, mucosal scrapings, semen, tissue biopsy and saliva.

6. The method of claim 1, wherein the dog is selected from the group consisting of akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, Labrador retrievers, lowchen, miniature poodle, miniature schnauzer, Nova scotia duck tolling retriever, Portuguese water dogs, samoyed, silky terrier, spitz, standard poodle, standard wirehaired dachshund, Tibetan terriers and toy poodle.

* * * * *